United States Patent
Klar et al.

(10) Patent No.: US 11,781,136 B2
(45) Date of Patent: Oct. 10, 2023

(54) OLIGONUCLEOTIDE INHIBITING THE EXPRESSION OF CHOP

(71) Applicant: Secarna Pharmaceuticals GmbH & Co. KG, Marburg (DE)

(72) Inventors: Richard Klar, Munich (DE); Frank Jaschinski, Puchheim (DE); Sven Michel, Bernried (DE)

(73) Assignee: Secarna Pharmaceuticals GmbH & Co. KG, Marburg (DE)

( * ) Notice: Subject to any disclaimer, the term of this patent is extended or adjusted under 35 U.S.C. 154(b) by 39 days.

(21) Appl. No.: 16/651,458

(22) PCT Filed: Sep. 28, 2018

(86) PCT No.: PCT/EP2018/076470
§ 371 (c)(1),
(2) Date: Mar. 27, 2020

(87) PCT Pub. No.: WO2019/063792
PCT Pub. Date: Apr. 4, 2019

(65) Prior Publication Data
US 2020/0283764 A1 Sep. 10, 2020

(30) Foreign Application Priority Data
Sep. 28, 2017 (EP) ..................................... 17193792

(51) Int. Cl.
*C07H 21/04* (2006.01)
*C12N 15/113* (2010.01)
*A61P 35/00* (2006.01)
*A61K 45/06* (2006.01)

(52) U.S. Cl.
CPC ............ *C12N 15/113* (2013.01); *A61P 35/00* (2018.01); *A61K 45/06* (2013.01); *C12N 2310/11* (2013.01); *C12N 2310/3231* (2013.01)

(58) Field of Classification Search
None
See application file for complete search history.

(56) References Cited

U.S. PATENT DOCUMENTS 9,752,145 B2 * 9/2017 Rodriguez ............ C12N 15/113
2015/0368648 A1 12/2015 Bhandari

FOREIGN PATENT DOCUMENTS

| EP | 2213738 A2 | 8/2010 |
| WO | 2008029414 A2 | 3/2008 |
| WO | 2015142713 A1 | 9/2015 |

OTHER PUBLICATIONS

Miyagishi et al. (Antisense and Nucleic Acid Drug Development, 2003, 13:1-7).*
Vickers et al. (The Journal of Biological Chemistry, 2003, 278:7108-7118, citation of record).*
Dean et al. (Oncogene, 2003, 22:9087-9096).*
Nishitoh, Hideki. "CHOP is a multifunctional transcription factor in the ER stress response." The Journal of Biochemistry 151.3 (2012): 217-219.*
Wang, Li-Le, et al. "CHOP overexpression sensitizes human non-small cell lung cancer cells to cisplatin treatment by Bcl-2/JNK pathway." American Journal of Translational Research 13.6 (2021): 6279.*
Hattori et al., "CHOP, a Basic Leucine Zipper Transcriptional Factor, Contributes to the Antiproliferative Effect of IL-1 on A375 Human Melanoma Cells Through Augmenting Transcription of IL-6", Journal of Interferon & Cytokine Reseach, vol. 21, Issue 5, pp. 323-332, 2001 DOI: 10.1089/107999001300177510.
Van Der Sanden et al., "Induction of CCAAT/Enhancer-binding Protein (C/EBP)-homologous Protein/Growth Arrest and DNA Damage-inducible Protein 153 Expression during Inhibition of Phosphatidylcholine Synthesis Is Mediated via Activation of a C/EBP-activating Transcription Factor-responsive Element", The Journal of Biological Chemistry, 2004, vol. 279, No. 50, Issue of Dec. 10, pp. 52007-52015.
Yang, Y. et al., "Transcription Factor C/EBP Homologous Protein in Health and Diseases" Fronteirs in Immunology, Nov. 27, 2017, vol. 8, Article 1612, 18 pgs.
Hetz, C. et al., "Targeting the unfolded protein response in disease", Nature Reviews Drug Discovery, Sep. 2013, vol. 12, pp. 703-719.
Cao, Y. et al., "ER stress-induced mediator C/EBP homologous protein thwarts effector T cell activity in tumors through T-bet repression", Nature Communications, 2019, 10:1280, 15 pgs.
Thevenot, P.T. et al., "The stress-response sensor Chop regulates the function and accumlation of myeloid-derived suppressor cells in tumors", Immunity, Sep. 18, 2014, 41(3), 28 pgs.
Shahzad, K. et al., "CHOP-ASO Ameliorates Glomerular and Tubular Damage on Top of ACE Inhibition in Diabetic Kidney Disease", JASN, 32, 2021, pp. 3066-3079.

* cited by examiner

*Primary Examiner* — Kimberly Chong
(74) *Attorney, Agent, or Firm* — Verrill Dana, LLP

(57) ABSTRACT

The present invention refers to an inhibitor consisting of oligonucleotides comprising 10 to 25 nucleotides, wherein at least one of the nucleotides is modified, and the oligonucleotide hybridizes with a nucleic acid sequence of C/EBP-homologous protein (Chop) of SEQ ID NO.1 (human) and/or SEQ ID NO. 48 (human) but also with mouse and rat sequences, wherein the oligonucleotide N inhibits at least 50% of the Chop expression. The invention is further directed to a pharmaceutical composition comprising such oligonucleotide.

12 Claims, 16 Drawing Sheets
Specification includes a Sequence Listing.

Fig. 1: Chop mRNA sequence of NM_001195053 (SEQ ID NO. 1)

GAGGTCAGAGACTTAAGTCTAAGGCACTGAGCGTATCATGTTAAAGATGAGCGGGT
GGCAGCGACAGAGCCAAAATCAGAGCTGGAACCTGAGGAGAGAGTGTTCAAGAAGG
AAGTGTATCTTCATACATCACCACACCTGAAAGCAGCACCAAAGCAGCCATAAACAA
TATGTAAATAAACAGATGTGGCTGTATTCCAGTACAACTTTACCTACAAAAACAGGC
ATCAGACCAGCTTGCCAACTTGTGGCATAGACTGTTTGCTACATGGAGCTTGTTCCA
GCCACTCCCCATTATCCTGCAGATGTGCTTTTCCAGACTGATCCAACTGCAGAGATG
GCAGCTGAGTCATTGCCTTTCTCCTTCGGGACACTGTCCAGCTGGGAGCTGGAAGC
CTGGTATGAGGACCTGCAAGAGGTCCTGTCTTCAGATGAAAATGGGGGTACCTATG
TTTCACCTCCTGGAAATGAAGAGGAAGAATCAAAAATCTTCACCACTCTTGACCCTG
CTTCTCTGGCTTGGCTGACTGAGGAGGAGCCAGAACCAGCAGAGGTCACAAGCACC
TCCCAGAGCCCTCACTCTCCAGATTCCAGTCAGAGCTCCCTGGCTCAGGAGGAAGA
GGAGGAAGACCAAGGGAGAACCAGGAAACGGAAACAGAGTGGTCATTCCCCAGCCC
GGGCTGGAAAGCAGCGCATGAAGGAGAAAGAACAGGAGAATGAAAGGAAAGTGGC
ACAGCTAGCTGAAGAGAATGAACGGCTCAAGCAGGAAATCGAGCGCCTGACCAGGG
AAGTAGAGGCGACTCGCCGAGCTCTGATTGACCGAATGGTGAATCTGCACCAAGCA
TGAACAATTGGGAGCATCAGTCCCCCACTTGGGCCACACTACCCACCTTTCCCAGAA
GTGGCTACTGACTACCCTCTCACTAGTGCCAATGATGTGACCCTCAATCCCACATAC
GCAGGGGGAAGGCTTGGAGTAGACAAAAGGAAAGGTCTCAGCTTGTATATAGAGAT
TGTACATTTATTTATTACTGTCCCTATCTATTAAAGTGACTTTCTATGAGCCAAAAAA
AAAAAAAAA

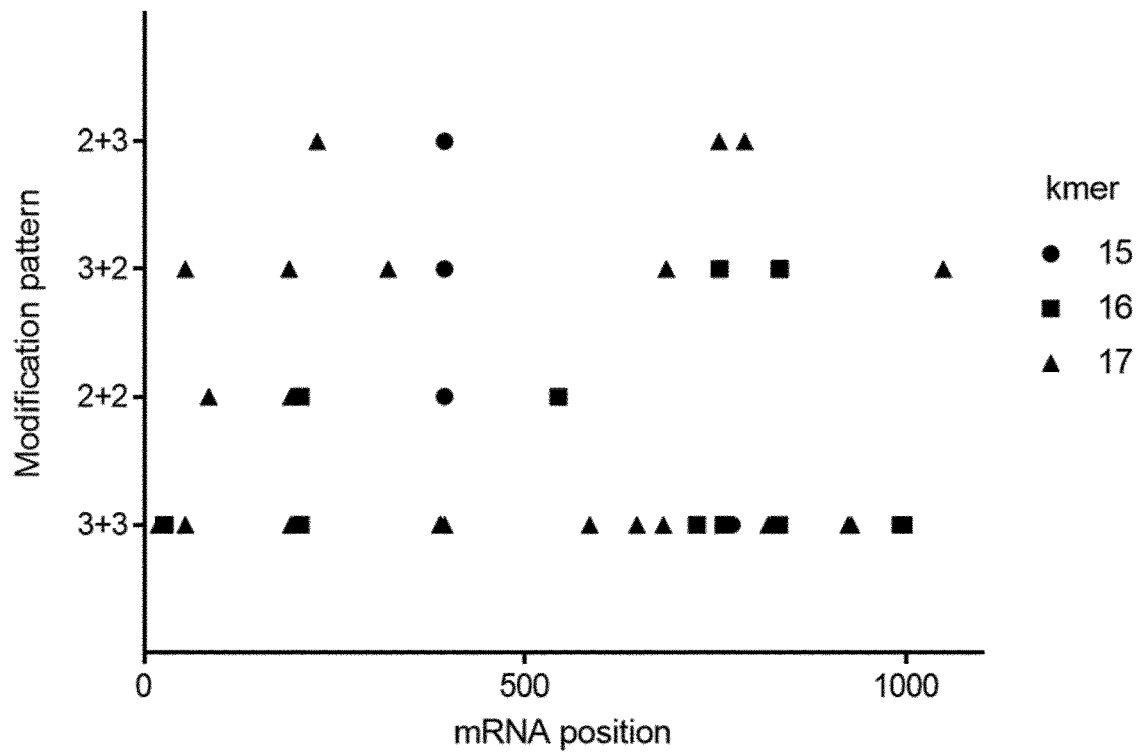

Fig. 2: Distribution of Chop antisense oligonucleotide binding sites on the Chop mRNA, length and modification pattern of Chop antisense oligonucleotides

Fig. 3A and 3B: First efficacy screening round of Chop antisense oligonucleotides in human cancer cell lines

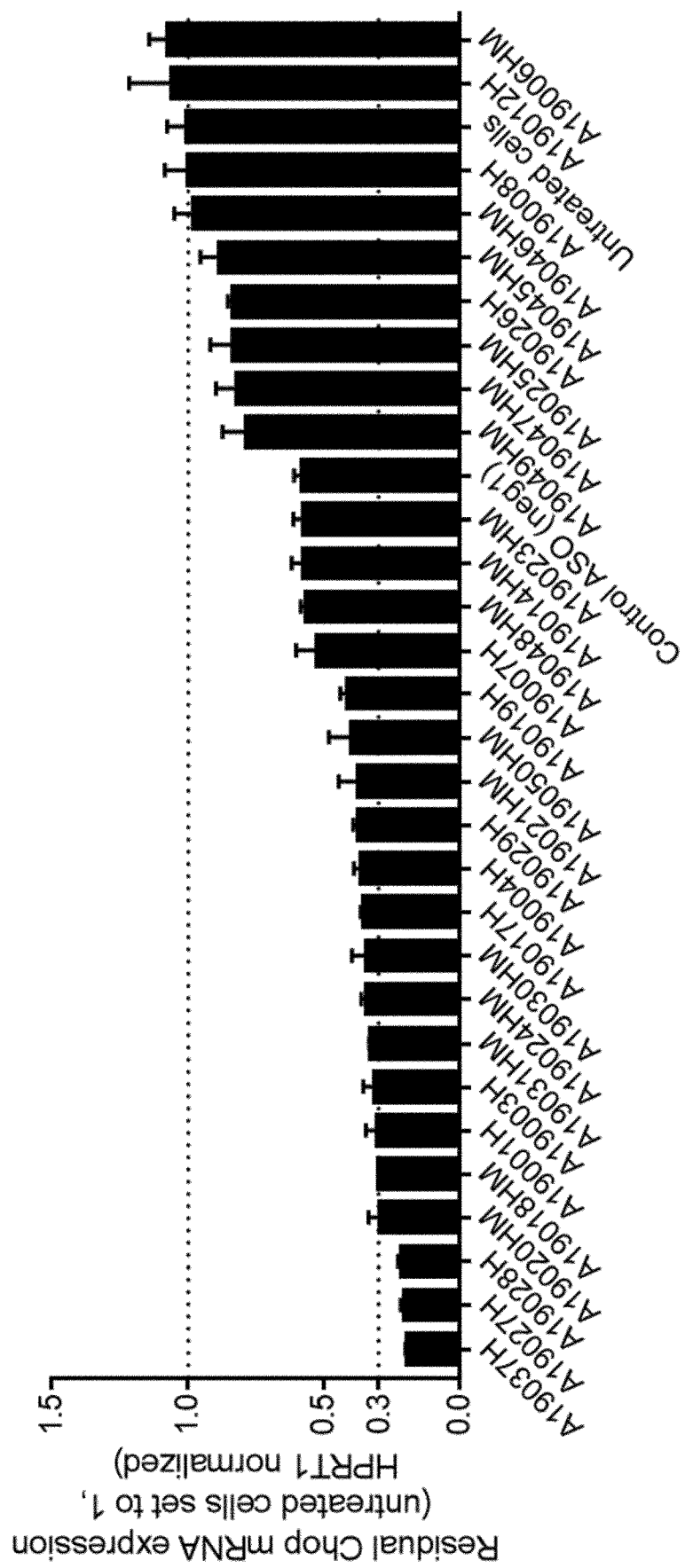
Fig. 4A and 4B: Second efficacy screening round of Chop antisense oligonucleotides in human cancer cell lines

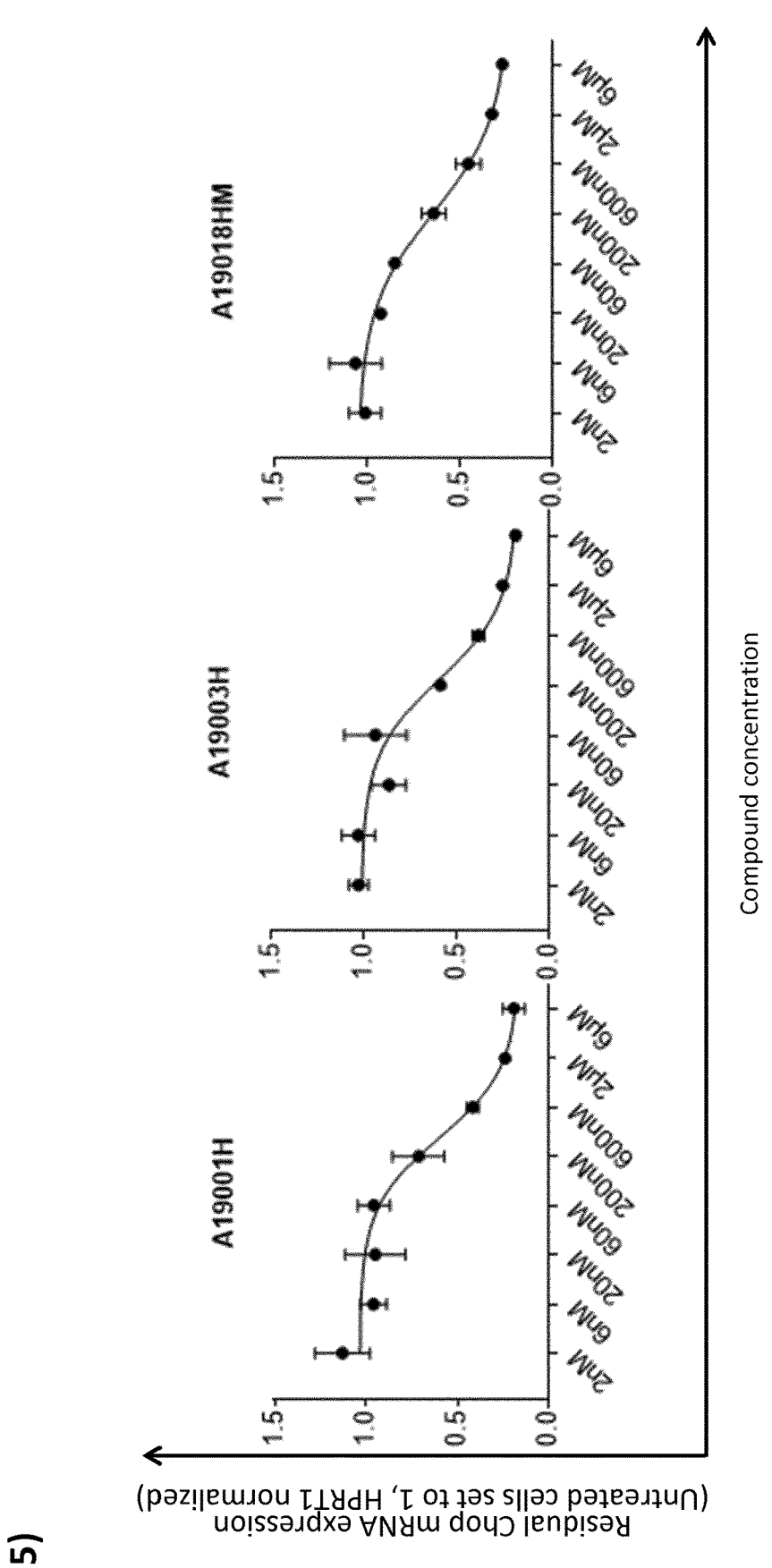
Fig. 5: Investigation of the dose-dependent Chop mRNA knockdown by selected Chop antisense oligonucleotides in EFO-21 cells

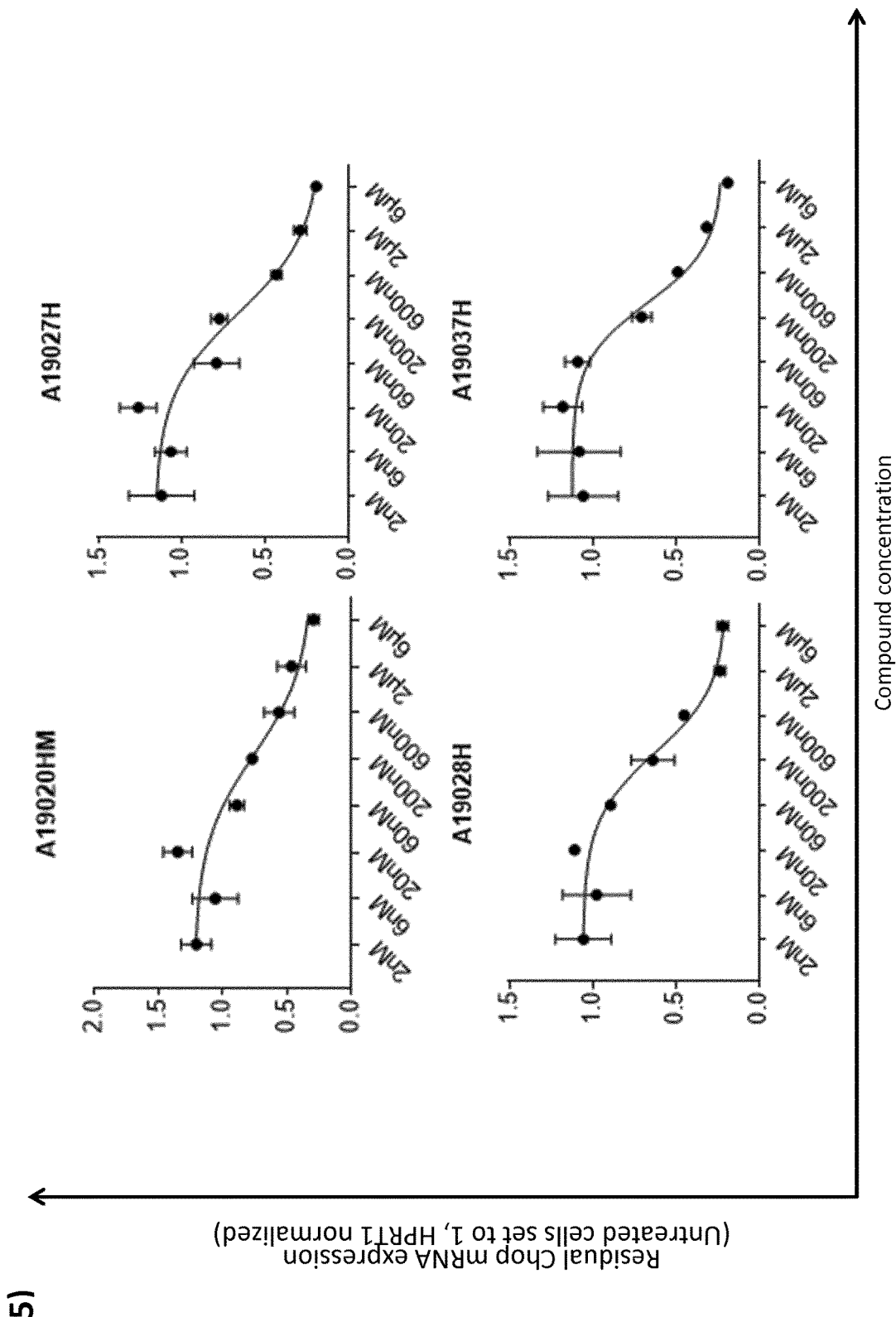
Fig. 5: Investigation of the dose-dependent Chop mRNA knockdown by selected Chop antisense oligonucleotides in EFO-21 cells (continued)

Fig. 6: Chop mRNA knockdown in activated human CD8+ T cells
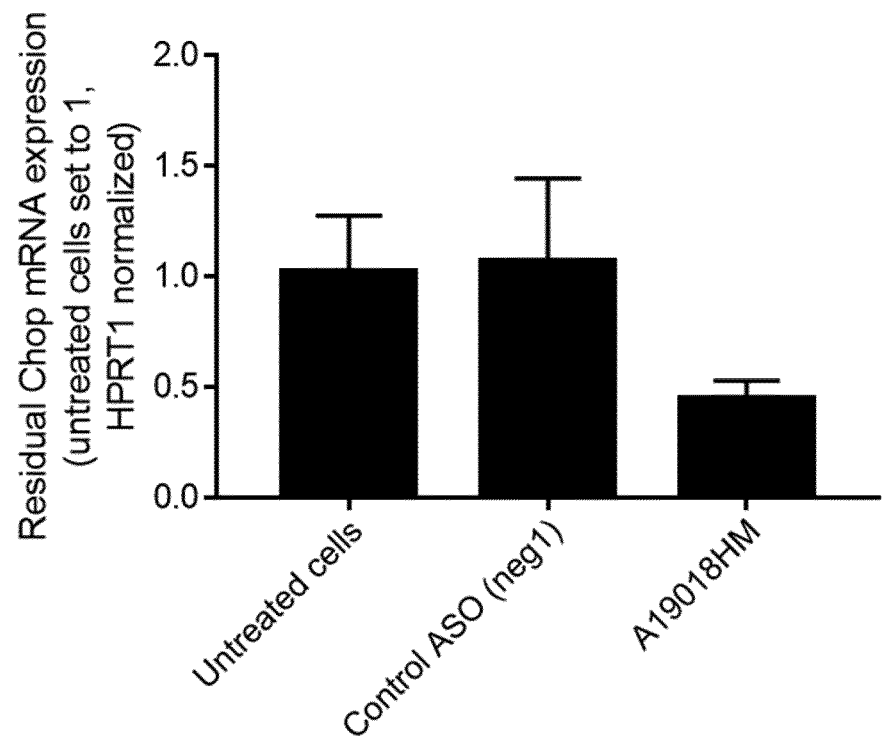

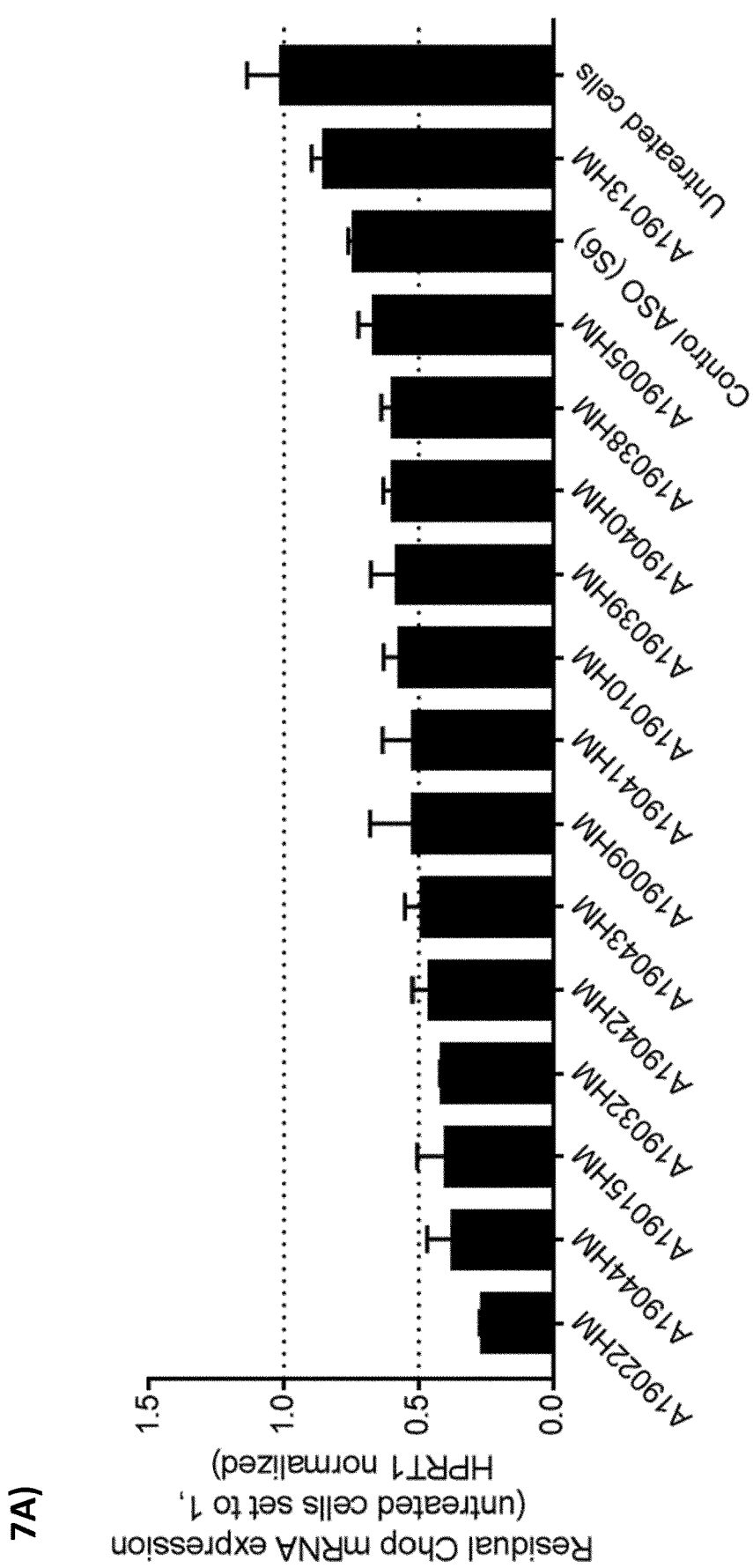
Fig. 7A and 7B: First efficacy screening round of Chop antisense oligonucleotides in murine cancer cell lines

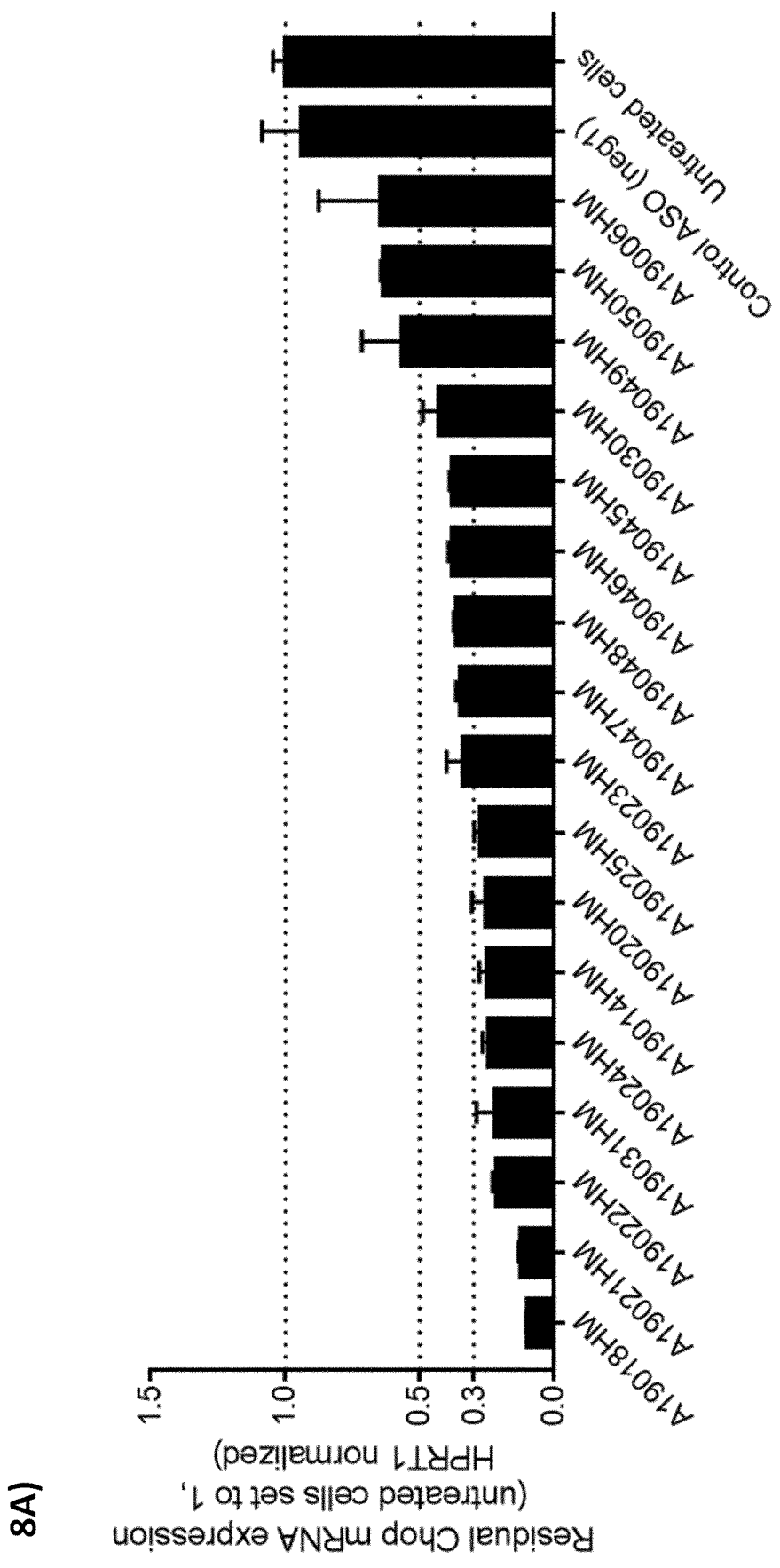
Fig. 8A and 8B: Second efficacy screening round of Chop antisense oligonucleotides in murine cancer cell lines

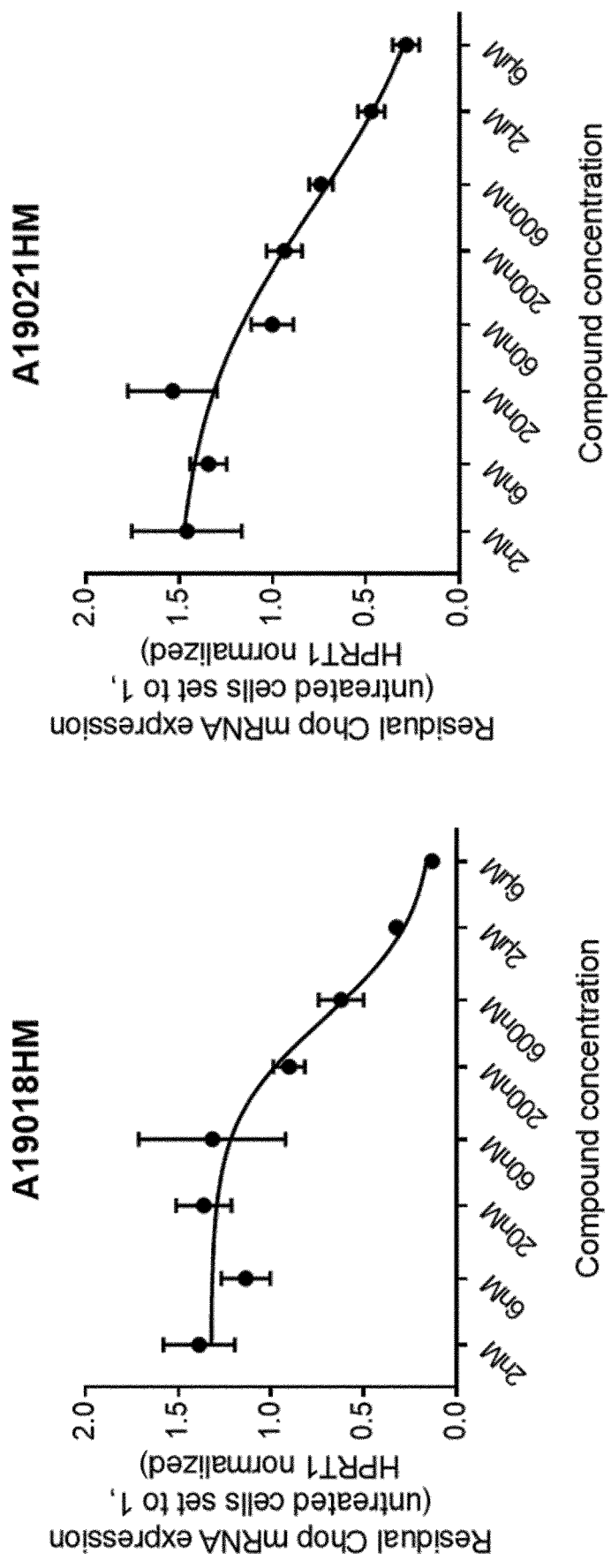
Fig. 9: Investigation of the dose-dependent Chop mRNA knockdown by selected Chop antisense oligonucleotides in Renca cells

Fig. 10: Knockdown of Chop in murine MDSC

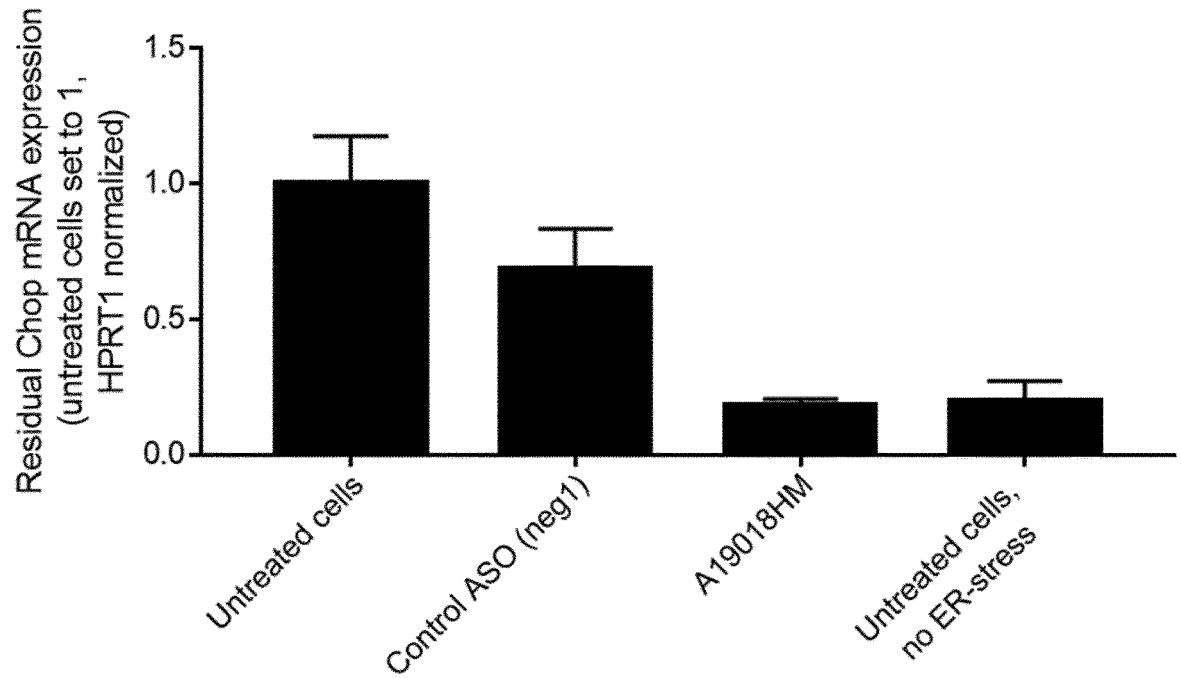

Fig. 11: Chop RNA sequence of ENST00000551116.5 (SEQ ID NO.48)

Intronic regions of Chop RNA ENST00000551116.5:

>ENST00000551116.5 intron 1:protein_coding
GCGAGTACTGATTCCCATCTACCTTTTACCCTCCCGTCTCCTCAAAGTTGGGGCGTC
CGCTCTTTAGGATCGGCCTCACTCCTCCACAGTGAAGTTAGGGACCGTCCGAGAGA
GGAATGGGGAGAGTCCCTTATTCTGGGGTGGTGCTTACAAACCCCTATTGCTTCGG
ACGACGGCGTCTCTCCACCCCTGCCCGGAGCCGGAACACGGGCCCTGCTCTGTGCT
GCTGGGCAAAGGGACCTCGGTTGCCCTTGGGAAATTCATTCTTTCCCGTAGCCAACT
TCAGGCCTCATCGTTAGGCCTGTCCGCGGGGAGGCAGGTCAGCAGGACACACCCCC
GCTCTAAGACTGGGTGACCATCGCTCAGGCCGTTTCCGCCGCTTCGCCACCAGCGG
GCCTTCTCCCTACCCCACCCCCAATTCTGTCTCAGTCTCAGTGCCTCTGGTGTCAGC
ATGGCCACCTTGGTAGCTGGGGCTACTGGACCCTGCAGCGGATAGGGGAACCTTGA
GGAGACACAAGCCTTTGGGAGGGGTGCCGATGGACAGGGAGTGGTGTGTTTTCCTT
TTGCCGTAGAGGTCTCTGGGCCTCCTGCACAAGAGAGCAGCCTGGATCTCTTAAGT
GTAGGAGGCCATTTGGGGTCTCCCCAGGGTATTGTCCTTCCCTCGGGATTAGTCCCT
GCCTCTTTAACCCGGTCCTGTCTCCCAGCTAATCTCTGTGTAACCATTGCATCAGGC
CAGCCCCGTTTGGCTCTGCAGCCTTCTGACCTGAGGCTCTACTGCTGATGAAAGCCA
AGTCCCACACACTGGAAGGCAAGGGAGGGTTCCCCAGGGAGGACAGCCCTGCAGG
AAATACTTCGGGCAATATTGCATCTCTAGCCCCTAGGGATCAGCAGCTGCCACTCTG

```
CTTCTGCCCCTTCCCTATAAGAGAGACTGGGGGGAGTTTATCCATTCATTCTTAACA
AATACTTAATGAGGACCTACTGTGTGCCACACAGTTTGGGGCTCAGGGTACATCCTT
GAGCAAGAGGAAAAAATCATCTCAGTGGGAGGCCTACAGTAAACAAAATATAAGTG
CCACGGAGAAAGCTAAAGCAGAGAAAGGAATGGAGAATGTTCAGGATGGAGGTCAG
AGTGTTACATCAGGTGGTCAGGAATTACCTTAGGTAATTCCTCCACTCAAAACCCTT
CAGTGACTTCCATGACATGAAATAGGAAGTCATTGGAGGGTTTGAGCAGAGGAATG
ACCTGTTTTAAAAGGCTCACTCAGGCTGCTGTATGGTGAATAGAGTTGCGGAGGGG
TGGCAAGAGAAGAAATGGGAAGACCTTCTGCAGTCAGAAAGTTTCTGCAGTAATTTA
GAGATGGTAGTGAATTGATCTAGATTGGAAACAATGGAATTAGAAGTGTTTAGATTC
TTCTAAGCAAAGGTTTTAAAAACTCATTTTTAAAGAATGAGTTAAGGGCCGGGCATG
GTGGCTCACACCTGTAATCCCAGCACTTTGGGAGACCAGAGGTGGGTGGATCACCT
GAGGTCAGGAGTTCAAGACCAGCCTGGCCAACATGGTGAAATCCCATCTTTACTAAA
AATACAAAAATTAGCCGGGCATGGCAGTGCATGCCTGTAATCCCAGCTACTCCGGA
GGCTGAAGCAGGAGAATCGCTTGAACCCAGCAGGCGGAGGTTGCAGTGAGCCGATT
GCGCCACTGCCTTCCAGCCTGGGCAAAAAGAGTGAGACCCGTCTCAGAAAAAAAGG
AATGAGTTAAAATTTGCTAGTACTTTGGATTGCAGGGTGTGAGAGAGGAATGAA
GGATGATACCAAGGTTTTTAGCTTAAGCAACTAGAGTTGTCATCTGAGATGGGGATG
ACCTTGGAAGGGGAAAATCAGCAAGAGTTTGCCTTTGCACATAGTCTTAGGTGCCTA
TTAGACATTGAAAAGAAATGGCAAGTAGGCAGTAGACAGCAGAGTCTGAAGTTCT
GGAAGAGGTCCAGACTGGAAATGTACATTTGGAGGATGTCAGCCCTGTGGGAATGG
AGTTAGGAAATGCTATGATTTGTTCCCTTCCCTGTAGTTTAGTTTTTACCCTGGCA
GATTTGAGGCCTGCTTTGGATTTAGAGAAAGCTGAGTTGGCCAGGACTTTACTATTA
TGTAACCAGGACTACAAATGTCAGCAACTAAAAATAAAGAAAGTCAGGCCCTCTTCT
GCCCTTCGAAATGGCTACAGGGACCAAGTATGCATACCCCACAAGACCAGAAGTAA
GGAAGGACCAGTAGGAGGCTGGAGGTAAAAGAAAAATAAGGGCCCAGCACGGTAG
CTCATGCCTATAATCCCAGCACTTTGGGAAGCGATGGATCACAAGGTTAAGAGATG
GAGACCATCCTGGCCAACATAGTGAAACCCTATCTCTGCTAAAAACACAAAAATTAG
CTGGGCGTGGTGGCACGCGCCTGTAGTCCCAGCTACTCGGGAGGCCGAGGCAGAA
GAATCACTTGAACCGAGGAGGCAGAGGTTGCAGTGAGCCGAGATCGCACCACTGCA
CTTCAGCCTGGCAACAGAGCAAGACTTGGTCTCAAAAAAAAAAAAAGAAAGAAAAA
AAGAAAAAGAAAAGTAAGTTGCCTCTCCCCCTTCCAAAAATGGCTGACATTTCTCTT
TGTTGCCCACAG

>ENST00000551116.5 intron 2:protein_coding
GTAAACTTAACCTACCCTTTTCCAAAAATTTTAAACGGCAGGACAGTAAATATTTTG
ATGTTAAAAGTCCTATAGTCTCTAGCGTGACTCTTCATCTCTGCCACTGTAG >ENST00000551116.5 intron 3:protein_coding
GTAAGAATGTTAGCCCTAAAGCTAAAGGGGATGTTACCTTTCCCTTCTCAACTAAA
TCTATGTTCCCTTTCCTCATTTCCTTGAAG
```

Cont. Fig. 11

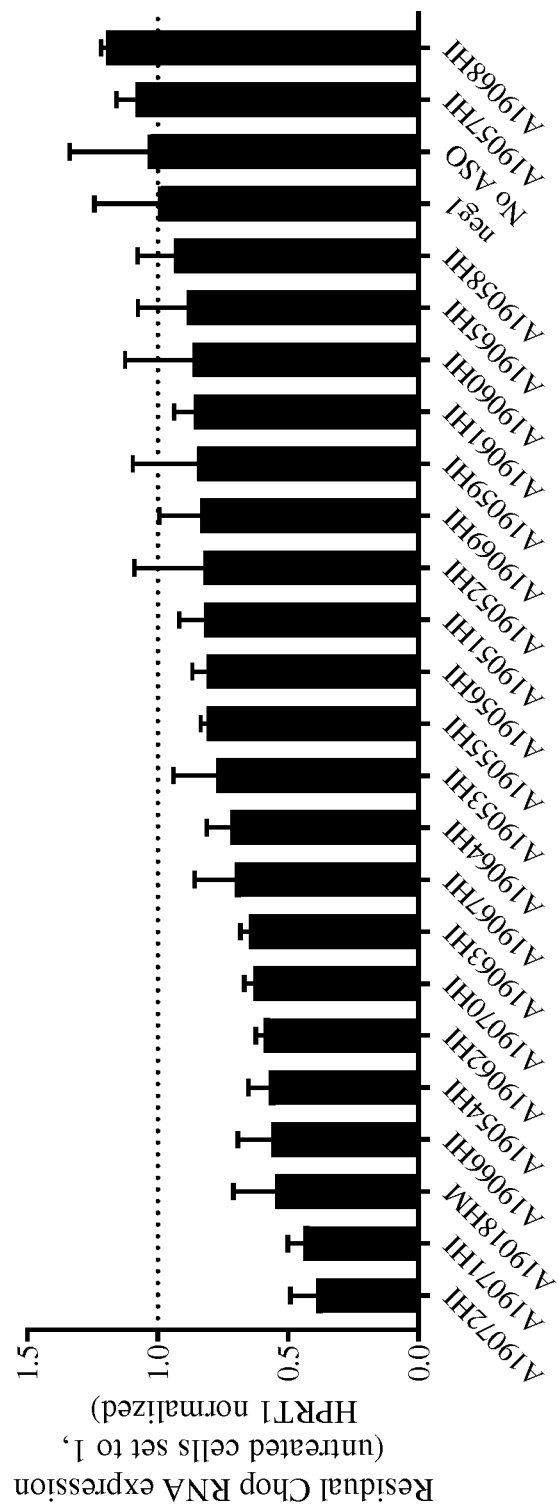
Fig. 12: Efficacy screening of intronic Chop antisense oligonucleotides in EFO-21 cells

SEQUENCE LISTING

<160> NUMBER OF SEQ ID NOS: 70

<210> SEQ ID NO 1
<211> LENGTH: 1081
<212> TYPE: DNA
<213> ORGANISM: Homo sapiens

<400> SEQUENCE: 1

```
gaggtcagag acttaagtct aaggcactga gcgtatcatg ttaaagatga gcgggtggca      60
gcgacagagc caaaatcaga gctggaacct gaggagagag tgttcaagaa ggaagtgtat     120
cttcatacat caccacacct gaaagcagca ccaaagcagc cataaacaat atgtaaataa     180
acagatgtgg ctgtattcca gtacaacttt acctacaaaa acaggcatca gaccagcttg     240
ccaacttgtg gcatagactg tttgctacat ggagcttgtt ccagccactc cccattatcc     300
tgcagatgtg ctttttccaga ctgatccaac tgcagagatg gcagctgagt cattgccttt     360
ctccttcggg acactgtcca gctgggagct ggaagcctgg tatgaggacc tgcaagaggt     420
cctgtcttca gatgaaaatg ggggtaccta tgtttcacct cctggaaatg aagaggaaga     480
atcaaaaatc ttcaccactc ttgaccctgc ttctctggct tggctgactg aggaggagcc     540
agaaccagca gaggtcacaa gcacctccca gagccctcac tctccagatt ccagtcagag     600
ctccctggct caggaggaag aggaggaaga ccaagggaga accaggaaac ggaaacagag     660
tggtcattcc ccagcccggg ctggaaagca gcgcatgaag gagaaagaac aggagaatga     720
aaggaaagtg gcacagctag ctgaagagaa tgaacggctc aagcaggaaa tcgagcgcct     780
gaccagggaa gtagaggcga ctcgccgagc tctgattgac cgaatggtga atctgccacca     840
agcatgaaca attgggagca tcagtccccc acttgggcca cactacccac ctttcccaga     900
agtggctact gactaccctc tcactagtgc caatgatgtg accctcaatc ccacatacgc     960
aggggaagg cttggagtag acaaaaggaa aggtctcagc ttgtatatag agattgtaca    1020
tttatttatt actgtcccta tctattaaag tgactttcta tgagccaaaa aaaaaaaaaa    1080
a                                                                    1081
```

<210> SEQ ID NO 2
<211> LENGTH: 16
<212> TYPE: DNA
<213> ORGANISM: Artificial Sequence
<220> FEATURE:
<223> OTHER INFORMATION: antisense oligonucleotide

```
<400> SEQUENCE: 2
ctagctgtgc cacttt                                                  16

<210> SEQ ID NO 3
<211> LENGTH: 16
<212> TYPE: DNA
<213> ORGANISM: Artificial Sequence
<220> FEATURE:
<223> OTHER INFORMATION: antisense oligonucleotide

<400> SEQUENCE: 3
tttcctgctt gagccg                                                  16

<210> SEQ ID NO 4
<211> LENGTH: 16
<212> TYPE: DNA
<213> ORGANISM: Artificial Sequence
<220> FEATURE:
<223> OTHER INFORMATION: antisense oligonucleotide

<400> SEQUENCE: 4
acatgatacg ctcagt                                                  16

<210> SEQ ID NO 5
<211> LENGTH: 17
<212> TYPE: DNA
<213> ORGANISM: Artificial Sequence
<220> FEATURE:
<223> OTHER INFORMATION: antisense oligonucleotide

<400> SEQUENCE: 5
cagattcacc attcggt                                                 17

<210> SEQ ID NO 6
<211> LENGTH: 17
<212> TYPE: DNA
<213> ORGANISM: Artificial Sequence
<220> FEATURE:
<223> OTHER INFORMATION: antisense oligonucleotide

<400> SEQUENCE: 6
atgcttggtg cagattc                                                 17

<210> SEQ ID NO 7
<211> LENGTH: 16
<212> TYPE: DNA
<213> ORGANISM: Artificial Sequence
<220> FEATURE:
<223> OTHER INFORMATION: antisense oligonucleotide

<400> SEQUENCE: 7
tctatataca agctga                                                  16

<210> SEQ ID NO 8
<211> LENGTH: 17
<212> TYPE: DNA
<213> ORGANISM: Artificial Sequence
<220> FEATURE:
<223> OTHER INFORMATION: antisense oligonucleotide

<400> SEQUENCE: 8
tacgctcagt gccttag                                                 17

<210> SEQ ID NO 9
```

```
<211> LENGTH: 17
<212> TYPE: DNA
<213> ORGANISM: Artificial Sequence
<220> FEATURE:
<223> OTHER INFORMATION: antisense oligonucleotide

<400> SEQUENCE: 9
tgatacgctc agtgcct                                                    17

<210> SEQ ID NO 10
<211> LENGTH: 17
<212> TYPE: DNA
<213> ORGANISM: Artificial Sequence
<220> FEATURE:
<223> OTHER INFORMATION: antisense oligonucleotide

<400> SEQUENCE: 10
gttcatgctt ggtgcag                                                    17

<210> SEQ ID NO 11
<211> LENGTH: 15
<212> TYPE: DNA
<213> ORGANISM: Artificial Sequence
<220> FEATURE:
<223> OTHER INFORMATION: antisense oligonucleotide

<400> SEQUENCE: 11
tcaggcgctc gattt                                                      15

<210> SEQ ID NO 12
<211> LENGTH: 16
<212> TYPE: DNA
<213> ORGANISM: Artificial Sequence
<220> FEATURE:
<223> OTHER INFORMATION: antisense oligonucleotide

<400> SEQUENCE: 12
ttcatgcttg gtgcag                                                     16

<210> SEQ ID NO 13
<211> LENGTH: 17
<212> TYPE: DNA
<213> ORGANISM: Artificial Sequence
<220> FEATURE:
<223> OTHER INFORMATION: antisense oligonucleotide

<400> SEQUENCE: 13
ccttcatgcg ctgcttt                                                    17

<210> SEQ ID NO 14
<211> LENGTH: 16
<212> TYPE: DNA
<213> ORGANISM: Artificial Sequence
<220> FEATURE:
<223> OTHER INFORMATION: antisense oligonucleotide

<400> SEQUENCE: 14
ctcgatttcc tgcttg                                                     16

<210> SEQ ID NO 15
<211> LENGTH: 16
<212> TYPE: DNA
<213> ORGANISM: Artificial Sequence
<220> FEATURE:
<223> OTHER INFORMATION: antisense oligonucleotide
```

```
<400> SEQUENCE: 15
gttcatgctt ggtgca                                                    16

<210> SEQ ID NO 16
<211> LENGTH: 17
<212> TYPE: DNA
<213> ORGANISM: Artificial Sequence
<220> FEATURE:
<223> OTHER INFORMATION: antisense oligonucleotide

<400> SEQUENCE: 16
acatcattgg cactagt                                                   17

<210> SEQ ID NO 17
<211> LENGTH: 17
<212> TYPE: DNA
<213> ORGANISM: Artificial Sequence
<220> FEATURE:
<223> OTHER INFORMATION: antisense oligonucleotide

<400> SEQUENCE: 17
ccactctgtt tccgttt                                                   17

<210> SEQ ID NO 18
<211> LENGTH: 16
<212> TYPE: DNA
<213> ORGANISM: Artificial Sequence
<220> FEATURE:
<223> OTHER INFORMATION: antisense oligonucleotide

<400> SEQUENCE: 18
aacatgatac gctcag                                                    16

<210> SEQ ID NO 19
<211> LENGTH: 17
<212> TYPE: DNA
<213> ORGANISM: Artificial Sequence
<220> FEATURE:
<223> OTHER INFORMATION: antisense oligonucleotide

<400> SEQUENCE: 19
tcatgcttgg tgcagat                                                   17

<210> SEQ ID NO 20
<211> LENGTH: 15
<212> TYPE: DNA
<213> ORGANISM: Artificial Sequence
<220> FEATURE:
<223> OTHER INFORMATION: antisense oligonucleotide

<400> SEQUENCE: 20
tcgatttcct gcttg                                                     15

<210> SEQ ID NO 21
<211> LENGTH: 16
<212> TYPE: DNA
<213> ORGANISM: Artificial Sequence
<220> FEATURE:
<223> OTHER INFORMATION: antisense oligonucleotide

<400> SEQUENCE: 21
tatacaagct gagacc                                                    16

<210> SEQ ID NO 22
```

```
<211> LENGTH: 17
<212> TYPE: DNA
<213> ORGANISM: Artificial Sequence
<220> FEATURE:
<223> OTHER INFORMATION: antisense oligonucleotide

<400> SEQUENCE: 22
ggtcacatca ttggcac                                                   17

<210> SEQ ID NO 23
<211> LENGTH: 17
<212> TYPE: DNA
<213> ORGANISM: Artificial Sequence
<220> FEATURE:
<223> OTHER INFORMATION: antisense oligonucleotide

<400> SEQUENCE: 23
tttacctcca gcctcct                                                   17

<210> SEQ ID NO 24
<211> LENGTH: 16
<212> TYPE: DNA
<213> ORGANISM: Artificial Sequence
<220> FEATURE:
<223> OTHER INFORMATION: antisense oligonucleotide

<400> SEQUENCE: 24
gttcatgctt ggtgca                                                    16

<210> SEQ ID NO 25
<211> LENGTH: 17
<212> TYPE: DNA
<213> ORGANISM: Artificial Sequence
<220> FEATURE:
<223> OTHER INFORMATION: antisense oligonucleotide

<400> SEQUENCE: 25
tttcctgctt gagccgt                                                   17

<210> SEQ ID NO 26
<211> LENGTH: 17
<212> TYPE: DNA
<213> ORGANISM: Artificial Sequence
<220> FEATURE:
<223> OTHER INFORMATION: antisense oligonucleotide

<400> SEQUENCE: 26
tcataccagg cttccag                                                   17

<210> SEQ ID NO 27
<211> LENGTH: 17
<212> TYPE: DNA
<213> ORGANISM: Artificial Sequence
<220> FEATURE:
<223> OTHER INFORMATION: antisense oligonucleotide

<400> SEQUENCE: 27
tatatacaag ctgagac                                                   17

<210> SEQ ID NO 28
<211> LENGTH: 17
<212> TYPE: DNA
<213> ORGANISM: Artificial Sequence
<220> FEATURE:
<223> OTHER INFORMATION: antisense oligonucleotide
```

<400> SEQUENCE: 28
cataccaggc ttccagc                                                    17

<210> SEQ ID NO 29
<211> LENGTH: 17
<212> TYPE: DNA
<213> ORGANISM: Artificial Sequence
<220> FEATURE:
<223> OTHER INFORMATION: antisense oligonucleotide

<400> SEQUENCE: 29
tggcaagctg gtctgat                                                    17

<210> SEQ ID NO 30
<211> LENGTH: 17
<212> TYPE: DNA
<213> ORGANISM: Artificial Sequence
<220> FEATURE:
<223> OTHER INFORMATION: antisense oligonucleotide

<400> SEQUENCE: 30
atccaggctg ctctctt                                                    17

<210> SEQ ID NO 31
<211> LENGTH: 17
<212> TYPE: DNA
<213> ORGANISM: Artificial Sequence
<220> FEATURE:
<223> OTHER INFORMATION: antisense oligonucleotide

<400> SEQUENCE: 31
catgcgctgc tttccag                                                    17

<210> SEQ ID NO 32
<211> LENGTH: 17
<212> TYPE: DNA
<213> ORGANISM: Artificial Sequence
<220> FEATURE:
<223> OTHER INFORMATION: antisense oligonucleotide

<400> SEQUENCE: 32
cactctgttt ccgtttc                                                    17

<210> SEQ ID NO 33
<211> LENGTH: 15
<212> TYPE: DNA
<213> ORGANISM: Artificial Sequence
<220> FEATURE:
<223> OTHER INFORMATION: antisense oligonucleotide

<400> SEQUENCE: 33
caggcgctcg atttc                                                      15

<210> SEQ ID NO 34
<211> LENGTH: 17
<212> TYPE: DNA
<213> ORGANISM: Artificial Sequence
<220> FEATURE:
<223> OTHER INFORMATION: antisense oligonucleotide

<400> SEQUENCE: 34
ctctgactgg aatctgg                                                    17

<210> SEQ ID NO 35

<211> LENGTH: 17
<212> TYPE: DNA
<213> ORGANISM: Artificial Sequence
<220> FEATURE:
<223> OTHER INFORMATION: antisense oligonucleotide

<400> SEQUENCE: 35
gctctgtcgc tgccacc                                                  17

<210> SEQ ID NO 36
<211> LENGTH: 15
<212> TYPE: DNA
<213> ORGANISM: Artificial Sequence
<220> FEATURE:
<223> OTHER INFORMATION: antisense oligonucleotide

<400> SEQUENCE: 36
tcctcatacc aggct                                                    15

<210> SEQ ID NO 37
<211> LENGTH: 17
<212> TYPE: DNA
<213> ORGANISM: Artificial Sequence
<220> FEATURE:
<223> OTHER INFORMATION: antisense oligonucleotide

<400> SEQUENCE: 37
gctctgtcgc tgccacc                                                  17

<210> SEQ ID NO 38
<211> LENGTH: 17
<212> TYPE: DNA
<213> ORGANISM: Artificial Sequence
<220> FEATURE:
<223> OTHER INFORMATION: antisense oligonucleotide

<400> SEQUENCE: 38
ccaggctgct ctcttgt                                                  17

<210> SEQ ID NO 39
<211> LENGTH: 17
<212> TYPE: DNA
<213> ORGANISM: Artificial Sequence
<220> FEATURE:
<223> OTHER INFORMATION: antisense oligonucleotide

<400> SEQUENCE: 39
ccaggctgct ctcttgt                                                  17

<210> SEQ ID NO 40
<211> LENGTH: 17
<212> TYPE: DNA
<213> ORGANISM: Artificial Sequence
<220> FEATURE:
<223> OTHER INFORMATION: antisense oligonucleotide

<400> SEQUENCE: 40
cgagtcgcct ctacttc                                                  17

<210> SEQ ID NO 41
<211> LENGTH: 17
<212> TYPE: DNA
<213> ORGANISM: Artificial Sequence
<220> FEATURE:
<223> OTHER INFORMATION: antisense oligonucleotide

```
<400> SEQUENCE: 41
ggtcctcata ccaggct                                                  17

<210> SEQ ID NO 42
<211> LENGTH: 16
<212> TYPE: DNA
<213> ORGANISM: Artificial Sequence
<220> FEATURE:
<223> OTHER INFORMATION: antisense oligonucleotide

<400> SEQUENCE: 42
caggctgctc tcttgt                                                   16

<210> SEQ ID NO 43
<211> LENGTH: 17
<212> TYPE: DNA
<213> ORGANISM: Artificial Sequence
<220> FEATURE:
<223> OTHER INFORMATION: antisense oligonucleotide

<400> SEQUENCE: 43
tctgcagttg gatcagt                                                  17

<210> SEQ ID NO 44
<211> LENGTH: 16
<212> TYPE: DNA
<213> ORGANISM: Artificial Sequence
<220> FEATURE:
<223> OTHER INFORMATION: antisense oligonucleotide

<400> SEQUENCE: 44
gtgacctctg ctggtt                                                   16

<210> SEQ ID NO 45
<211> LENGTH: 17
<212> TYPE: DNA
<213> ORGANISM: Artificial Sequence
<220> FEATURE:
<223> OTHER INFORMATION: antisense oligonucleotide

<400> SEQUENCE: 45
actctctcct caggttc                                                  17

<210> SEQ ID NO 46
<211> LENGTH: 18
<212> TYPE: DNA
<213> ORGANISM: Artificial Sequence
<220> FEATURE:
<223> OTHER INFORMATION: negative control

<400> SEQUENCE: 46
cgtttaggct atgtactt                                                 18

<210> SEQ ID NO 47
<211> LENGTH: 17
<212> TYPE: DNA
<213> ORGANISM: Artificial Sequence
<220> FEATURE:
<223> OTHER INFORMATION: S6 control

<400> SEQUENCE: 47
tctatcgtga tgtttct                                                  17

<210> SEQ ID NO 48
```

```
<211> LENGTH: 2858
<212> TYPE: DNA
<213> ORGANISM: Homo sapiens
<220> FEATURE:
<221> NAME/KEY: Intron
<222> LOCATION: (1)..(2662)
<223> OTHER INFORMATION: intron 1
<220> FEATURE:
<221> NAME/KEY: Intron
<222> LOCATION: (2663)..(2771)
<223> OTHER INFORMATION: intron 2
<220> FEATURE:
<221> NAME/KEY: Intron
<222> LOCATION: (2772)..(2858)
<223> OTHER INFORMATION: intron 3

<400> SEQUENCE: 48
```

| | | | | | |
|---|---|---|---|---|---|
| gcgagtactg | attcccatct | accttttacc | ctcccgtctc | ctcaaagttg | gggcgtccgc | 60 |
| tctttaggat | cggcctcact | cctccacagt | gaagttaggg | accgtccgag | agaggaatgg | 120 |
| ggagagtccc | ttattctggg | gtggtgctta | caaaccccta | ttgcttcgga | cgacggcgtc | 180 |
| tctccacccc | tgcccggagc | cggaacacgg | gccctgctct | gtgctgctgg | gcaaagggac | 240 |
| ctcggttgcc | cttgggaaat | tcattctttc | ccgtagccaa | cttcaggcct | catcgttagg | 300 |
| cctgtccgcg | gggaggcagg | tcagcaggac | acaccccgc | tctaagactg | ggtgaccatc | 360 |
| gctcaggccg | tttccgccgc | ttcgccacca | gcgggccttc | tccctacccc | accccaatt | 420 |
| ctgtctcagt | ctcagtgcct | ctggtgtcag | catggccacc | ttggtagctg | ggctactgg | 480 |
| accctgcagc | ggataggga | accttgagga | gacacaagcc | tttgggaggg | gtgccgatgg | 540 |
| acagggagtg | gtgtgttttc | cttttgccgt | agaggtctct | gggcctcctg | cacaagagag | 600 |
| cagcctggat | ctcttaagtg | taggaggcca | tttggggtct | ccccagggta | ttgtccttcc | 660 |
| ctcgggatta | gtccctgcct | ctttaacccg | gtcctgtctc | ccagctaatc | tctgtgtaac | 720 |
| cattgcatca | ggccagcccc | gtttggctct | gcagccttct | gacctgaggc | tctactgctg | 780 |
| atgaaagcca | agtcccacac | actggaaggc | aaggagggt | tccccaggga | ggacagccct | 840 |
| gcaggaaata | cttcgggcaa | tattgcatct | ctagccccta | gggatcagca | gctgccactc | 900 |
| tgcttctgcc | cctccctat | aagagagact | gggggagtt | tatccattca | ttcttaacaa | 960 |
| atacttaatg | aggacctact | gtgtgccaca | cagtttgggg | ctcagggtac | atccttgagc | 1020 |
| aagaggaaaa | aatcatctca | gtgggaggcc | tacagtaaac | aaaatataag | tgccacggag | 1080 |
| aaagctaaag | cagagaaagg | aatggagaat | gttcaggatg | gaggtcagag | tgttacatca | 1140 |
| ggtggtcagg | aattacctta | ggtaattcct | ccactcaaaa | cccttcagtg | acttccatga | 1200 |
| catgaaatag | gaagtcattg | gagggtttga | gcagaggaat | gacctgtttt | aaaaggctca | 1260 |
| ctcaggctgc | tgtatggtga | atagagttgc | ggaggggtgg | caagagaaga | aatgggaaga | 1320 |
| ccttctgcag | tcagaaagtt | tctgcagtaa | tttagagatg | gtagtgaatt | gatctagatt | 1380 |
| ggaaacaatg | gaattagaag | tgtttagatt | cttctaagca | aaggttttaa | aaactcattt | 1440 |
| ttaaagaatg | agttaagggc | cgggcatggt | ggctcacacc | tgtaatccca | gcactttggg | 1500 |
| agaccagagg | tgggtggatc | acctgaggtc | aggagttcaa | gaccagcctg | gccaacatgg | 1560 |
| tgaaatccca | tctttactaa | aaatacaaaa | attagccggg | catggcagtg | catgcctgta | 1620 |
| atcccagcta | ctccggaggc | tgaagcagga | gaatcgcttg | aacccagcag | gcggaggttg | 1680 |
| cagtgagccg | attgcgccac | tgccttccag | cctgggcaaa | aagagtgaga | cccgtctcag | 1740 |
| aaaaaaagga | atgagttaaa | atttgctagt | actttggatt | gcagggtgtg | agagagagga | 1800 |
| atgaaggatg | ataccaaggt | ttttagctta | agcaactaga | gttgtcatct | gagatgggga | 1860 |

```
tgaccttgga aggggaaaat cagcaagagt ttgcctttgc acatagtctt aggtgcctat    1920
tagacattga aaagaaatg gcaagtaggc agtagacagc agagtctgaa gttctggaag     1980
aggtccagac tggaaatgta catttggagg atgtcagccc tgtgggaatg gagttaggaa    2040
aatgctatga tttgttccct tccctgtagt ttagttttta ccctggcaga tttgaggcct    2100
gctttggatt tagagaaagc tgagttggcc aggactttac tattatgtaa ccaggactac    2160
aaatgtcagc aactaaaaat aaagaaagtc aggccctctt ctgcccttcg aaatggctac    2220
agggaccaag tatgcatacc ccacaagacc agaagtaagg aaggaccagt aggaggctgg    2280
aggtaaaaga aaaataaggg cccagcacgg tagctcatgc ctataatccc agcactttgg    2340
gaagcgatgg atcacaaggt taagagatgg agaccatcct ggccaacata gtgaaaccct    2400
atctctgcta aaaacacaaa aattagctgg gcgtggtggc acgcgcctgt agtcccagct    2460
actcgggagg ccgaggcaga agaatcactt gaaccgagga ggcagaggtt gcagtgagcc    2520
gagatcgcac cactgcactt cagcctggca acagagcaag acttggtctc aaaaaaaaaa    2580
aaagaaagaa aaaagaaaa agaaaagtaa gttgcctctc ccccttccaa aaatggctga     2640
catttctctt tgttgcccac aggtaaactt aacctaccct tttccaaaaa ttttaaacgg    2700
caggacagta aatattttga tgttaaaagt cctatagtct ctagcgtgac tcttcatctc    2760
tgccactgta ggtaagaatg ttagccctaa agctaaaggg ggatgttacc tttcccttct    2820
caactaaatc tatgttccct ttcctcattt ccttgaag                            2858

<210> SEQ ID NO 49
<211> LENGTH: 17
<212> TYPE: DNA
<213> ORGANISM: Artificial Sequence
<220> FEATURE:
<223> OTHER INFORMATION: antisense oligonucleotide

<400> SEQUENCE: 49
atcctaaaga gcggacg                                                   17

<210> SEQ ID NO 50
<211> LENGTH: 17
<212> TYPE: DNA
<213> ORGANISM: Artificial Sequence
<220> FEATURE:
<223> OTHER INFORMATION: antisense oligonucleotide

<400> SEQUENCE: 50
gtgaggccga tcctaaa                                                   17

<210> SEQ ID NO 51
<211> LENGTH: 17
<212> TYPE: DNA
<213> ORGANISM: Artificial Sequence
<220> FEATURE:
<223> OTHER INFORMATION: antisense oligonucleotide

<400> SEQUENCE: 51
agtgaggccg atcctaa                                                   17

<210> SEQ ID NO 52
<211> LENGTH: 17
<212> TYPE: DNA
<213> ORGANISM: Artificial Sequence
<220> FEATURE:
<223> OTHER INFORMATION: antisense oligonucleotide
```

```
<400> SEQUENCE: 52
attcctctct cggacgg                                                    17

<210> SEQ ID NO 53
<211> LENGTH: 17
<212> TYPE: DNA
<213> ORGANISM: Artificial Sequence
<220> FEATURE:
<223> OTHER INFORMATION: antisense oligonucleotide

<400> SEQUENCE: 53
gtcgtccgaa gcaatag                                                    17

<210> SEQ ID NO 54
<211> LENGTH: 17
<212> TYPE: DNA
<213> ORGANISM: Artificial Sequence
<220> FEATURE:
<223> OTHER INFORMATION: antisense oligonucleotide

<400> SEQUENCE: 54
ccgtcgtccg aagcaat                                                    17

<210> SEQ ID NO 55
<211> LENGTH: 17
<212> TYPE: DNA
<213> ORGANISM: Artificial Sequence
<220> FEATURE:
<223> OTHER INFORMATION: antisense oligonucleotide

<400> SEQUENCE: 55
gccgtcgtcc gaagcaa                                                    17

<210> SEQ ID NO 56
<211> LENGTH: 17
<212> TYPE: DNA
<213> ORGANISM: Artificial Sequence
<220> FEATURE:
<223> OTHER INFORMATION: antisense oligonucleotide

<400> SEQUENCE: 56
taacgatgag gcctgaa                                                    17

<210> SEQ ID NO 57
<211> LENGTH: 17
<212> TYPE: DNA
<213> ORGANISM: Artificial Sequence
<220> FEATURE:
<223> OTHER INFORMATION: antisense oligonucleotide

<400> SEQUENCE: 57
ggacaggcct aacgatg                                                    17

<210> SEQ ID NO 58
<211> LENGTH: 16
<212> TYPE: DNA
<213> ORGANISM: Artificial Sequence
<220> FEATURE:
<223> OTHER INFORMATION: antisense oligonucleotide

<400> SEQUENCE: 58
gacaggccta acgatg                                                     16

<210> SEQ ID NO 59
<211> LENGTH: 17
```

```
<212> TYPE: DNA
<213> ORGANISM: Artificial Sequence
<220> FEATURE:
<223> OTHER INFORMATION: antisense oligonucleotide

<400> SEQUENCE: 59
aacggcctga gcgatgg                                                   17

<210> SEQ ID NO 60
<211> LENGTH: 17
<212> TYPE: DNA
<213> ORGANISM: Artificial Sequence
<220> FEATURE:
<223> OTHER INFORMATION: antisense oligonucleotide

<400> SEQUENCE: 60
ggaaacggcc tgagcga                                                   17

<210> SEQ ID NO 61
<211> LENGTH: 17
<212> TYPE: DNA
<213> ORGANISM: Artificial Sequence
<220> FEATURE:
<223> OTHER INFORMATION: antisense oligonucleotide

<400> SEQUENCE: 61
gaagcggcgg aaacggc                                                   17

<210> SEQ ID NO 62
<211> LENGTH: 17
<212> TYPE: DNA
<213> ORGANISM: Artificial Sequence
<220> FEATURE:
<223> OTHER INFORMATION: antisense oligonucleotide

<400> SEQUENCE: 62
agagacctct acggcaa                                                   17

<210> SEQ ID NO 63
<211> LENGTH: 17
<212> TYPE: DNA
<213> ORGANISM: Artificial Sequence
<220> FEATURE:
<223> OTHER INFORMATION: antisense oligonucleotide

<400> SEQUENCE: 63
ggcctcctac acttaag                                                   17

<210> SEQ ID NO 64
<211> LENGTH: 17
<212> TYPE: DNA
<213> ORGANISM: Artificial Sequence
<220> FEATURE:
<223> OTHER INFORMATION: antisense oligonucleotide

<400> SEQUENCE: 64
tgaccacctg atgtaac                                                   17

<210> SEQ ID NO 65
<211> LENGTH: 17
<212> TYPE: DNA
<213> ORGANISM: Artificial Sequence
```

```
<220> FEATURE:
<223> OTHER INFORMATION: antisense oligonucleotide

<400> SEQUENCE: 65
taaggtaatt cctgacc                                                    17

<210> SEQ ID NO 66
<211> LENGTH: 17
<212> TYPE: DNA
<213> ORGANISM: Artificial Sequence
<220> FEATURE:
<223> OTHER INFORMATION: antisense oligonucleotide

<400> SEQUENCE: 66
cctgcaatcc aaagtac                                                    17

<210> SEQ ID NO 67
<211> LENGTH: 17
<212> TYPE: DNA
<213> ORGANISM: Artificial Sequence
<220> FEATURE:
<223> OTHER INFORMATION: antisense oligonucleotide

<400> SEQUENCE: 67
ttgtgatcca tcgcttc                                                    17

<210> SEQ ID NO 68
<211> LENGTH: 17
<212> TYPE: DNA
<213> ORGANISM: Artificial Sequence
<220> FEATURE:
<223> OTHER INFORMATION: antisense oligonucleotide

<400> SEQUENCE: 68
ccttgtgatc catcgct                                                    17

<210> SEQ ID NO 69
<211> LENGTH: 17
<212> TYPE: DNA
<213> ORGANISM: Artificial Sequence
<220> FEATURE:
<223> OTHER INFORMATION: antisense oligonucleotide

<400> SEQUENCE: 69
tactgtcctg ccgttta                                                    17

<210> SEQ ID NO 70
<211> LENGTH: 17
<212> TYPE: DNA
<213> ORGANISM: Artificial Sequence
<220> FEATURE:
<223> OTHER INFORMATION: antisense oligonucleotide

<400> SEQUENCE: 70
aagagtcacg ctagaga                                                    17
```

OLIGONUCLEOTIDE INHIBITING THE EXPRESSION OF CHOP

The present disclosure refers to an inhibitor of Chop expression consisting of an antisense oligonucleotide hybridizing with a nucleic acid sequence of C/EBP-homologous protein (Chop) mRNA and/or pre-mRNA, and to a pharmaceutical composition comprising such antisense oligonucleotide and a pharmaceutically acceptable carrier, excipient and/or dilutant.

BACKGROUND

C/EBP-homologous protein (Chop) is a member of the CCAAT/enhancer binding proteins (C/EBP) family of basic leucine zipper transcription factors, which is also known as growth arrest and DNA damage-inducible gene 153 (GADD153) (Back & Kaufman, *Annu. Reu. Biochem*, 2012, 81, 767-793). Chop consists of two functional domains, an N-terminal transcriptional activation domain and a C-terminal basic-leucine zipper (bZIP) domain (Li et al., *Acta Biochim Biophys*, 2014, 46 (8), 629-639).

While Chop is ubiquitously expressed at very low levels in the cytosol, its expression is induced in a wide variety of cells upon perturbations inducing endoplasmatic reticulum (ER) stress. This results in Chop accumulation in the nucleus (Ron & Habener, *Genes Dev.*, 1992, 6, 439-453). Factors inducing ER-stress are glucose deprivation, presumably by inhibiting N-linked protein glycosylation in the ER, amino acid starvation, tunicamycin, which blocks protein glycosylation, and dithiothreitol which disrupts disulfide bond formation. Accordingly, the human Chop promoter contains at least two stress response element motifs and one amino-acid-regulatory element motif for its transcriptional regulation. To achieve maximal induction of the CHOP promoter at ER stress, the interplay of three signaling pathways is required, which are the PKR-like endoplasmic reticulum kinase (PERK)/eIF2a signaling pathway, activating transcription factor 6a (ATF6) and Ire1/XBP-1 signaling pathway (Okada et al., *Biochem. J*, 2002, 366, 585-594).

Functionally, overexpression of Chop leads to cycle arrest and/or apoptosis. Chop downregulates the expression of anti-apoptotic protein factors such as Bcl-2 (Wang, *EMBO J.*, 1998, 17(13), 3619-3630), and activates expression of genes encoding pro-apoptotic proteins such as Caspase-3, BAX, GADD34, DOCs and EOR1alpha. Accordingly, induction of CHOP is involved in the development of various human diseases associated with severe ER stress and dysregulated apoptosis, such as neurodegenerative diseases, diabetes, ischemic diseases and acquired immune deficiency syndrome through cell loss (Li et al., *Acta Biochim Biophys*, 2014, 46 (8), 629-639). The ER-stress response has been demonstrated to be relevant in different diseases like diabetic nephropathy (DN), obesity, insulin resistance, type 2 diabetes mellitus and artheriosclerosis (Madhusudhan et al. 2015, Cnop et al. 2012, Back et al. 2012, Wang et al. 2012). Chop in particular has been shown to be involved in diabetic nephropathy (DN) and diabetes. More specifically, Chop knockout mice are protected from DN in a streptozotocin (STZ) induced diabetes model that reflects insulinopenic type 1 diabetes mellitus (Madhusudhan et al. 2015). Furthermore, in a model of type 2 diabetes (db/db mice) the genetic knockout of Chop results in improved glycemic control and expanded 6 cell mass by promoting 6 cell survival (Song et al. 2008).

Further, Chop plays an essential role in tumor derived immunosuppressive activity by inducing a state of T cell unresponsiveness toward tumor associated antigens (Gabrilouich & Nagaraj, *Nat. Rev. Immunol.*, 2009, 9(3), 162-174; Marigo et al., *Immunity*, 2010, 32, 790-802). Immune cells play an important role in the complex microenvironment of a tumor. On the one hand, there are immune effector cells like e.g. T cells or NK cells that are capable of recognizing immunogenic structures on the surface of tumor cells and thereby can attack tumor cells by the release of certain cytokines like e.g. interferon gamma (IFN-γ) or cytotoxic molecules like e.g. granzyme B. On the other hand, there are suppressive cells like e.g. regulatory T cells or myeloid-derived suppressor cells (MDSC), that produce cytokines like e.g. interleukin 10 (IL-10) or transforming growth factor beta (TGF-ß) and immunosuppressive enzymes like e.g. arginase. Those cytokines and enzymes have the capability to suppress the aforementioned immune effector cells. The expression of such suppressive factors is tightly regulated by transcription factors. In MDSC for example, the CCAAT/enhancer-binding protein-ß complex (C/EBPß) can activate the transcription of genes like IL-6 and arginase that contribute to the suppressive capacity of those cells (Corzo et al., 2009; Marigo et al., 2010; Sonda et al., 2013). C/EBPß contains a subdomain called C/EBPß liver-enriched inhibitory protein (LIP) that inhibits binding of the active C/EBPß complex (Hattori et al., 2003) to e.g. IL-6 and arginase promotors. C/EBP-homologous protein (Chop) binds to LIP and prevents its binding to the other domains of the C/EBPß complex, thereby allowing activation of the expression of e.g. IL-6 and arginase. Expression of Chop thereby contributes to the immunosuppressive activity of MDSC and is part of the endoplasmatic reticulum (ER)-stress response. The expression of Chop in MDSC has been shown to be induced by factors like e.g. reactive oxygen species (ROS) and peroxynitrite (PNT) in the tumor microenvironment (Thevenot et al. 2014).

As Chop is an intracellular factor with no enzymatic activity, inhibition of Chop by small molecules or antibodies are not or hardly suitable. Accordingly, an agent which is safe and effective in inhibiting the function of an intracellular mediator of immunosuppression like Chop is an important addition for the treatment of patients suffering from diseases or conditions affected for example by the activity of this factor.

So far no antisense oligonucleotide exists which is highly efficient in reduction and inhibition, respectively, of Chop expression and hybridizes with Chop mRNA and/or pre-mRNA. Studies with siRNA to inhibit Chop expression showed that in vivo inhibition is only possible if siRNA is packed in suitable packaging material. Even if siRNA is packed the efficiency on the inhibition of mRNA expression can often not be improved.

An oligonucleotide of the present invention is very successful in the inhibition of the expression of Chop. The mode of action of an oligonucleotide differs from the mode of action of an antibody or small molecule, and oligonucleotides are highly advantageous regarding for example
(i) the penetration of tumor tissue in solid tumors,
(ii) the blocking of multiple functions and activities, respectively, of a target,
(iii) the combination of oligonucleotides with each other or an antibody or a small molecule, and
(iv) the inhibition of intracellular effects which are not accessible for an antibody or inhibitable via a small molecule.

SUMMARY

The present invention refers to an inhibitor of the expression of Chop consisting of an antisense oligonucleotide comprising about 10 to 25 nucleotides, wherein at least one of the nucleotides is modified. The oligonucleotide hybridizes for example with a nucleic acid sequence of C/EBP-homologous protein (Chop) of SEQ ID NO.1 (human) and/or of SEQ ID NO.48 (human). The modified nucleotide is for example selected from the group consisting of a bridged nucleic acid (e.g., LNA, cET, ENA, 2'Fluoro modified nucleotide, 2'O-Methyl modified nucleotide or a combination thereof). In some embodiments, the oligonucleotide inhibits at least 50% of the Chop expression and in some embodiments the oligonucleotide inhibits the expression of Chop at a nanomolar concentration.

The present invention is further directed to a pharmaceutical composition comprising an antisense oligonucleotide of the present invention and optionally a pharmaceutically acceptable carrier, excipient, diluent or a combination thereof. In some embodiments, this pharmaceutical composition additionally comprises a chemotherapeutic such as platinum or gemcitabine, another disease specific active agent such as insulin, angiotensin-converting enzyme inhibitor, angiotensin receptor blocker, another oligonucleotide, an antibody, a HERA fusion protein, a ligand trap, a Fab fragment, a nanobody, a BiTe and/or a small molecule which is for example effective in tumor treatment, treatment of diabetes (e.g., insulin resistance, type 2 diabetes mellitus) and its side effects (e.g., diabetic nephropathy), treatment of obesity, treatment of nephrological diseases, and/or treatment of artheriosclerosis.

In some embodiments, the oligonucleotide of the present invention is in combination with another oligonucleotide, an antibody, a HERA fusion protein, a ligand trap, a Fab fragment, a nanobody, a BiTe and/or a small molecule, either each of these compounds is separate or combined in a pharmaceutical composition, wherein the oligonucleotide, the antibody and/or the small molecule inhibits or stimulates an immune suppressive factor such as IDO1, IDO2, CTLA-4, PD-1, PD-L1, LAG-3, VISTA, A2AR, CD39, CD73, STAT3, TDO2, TIM-3, TIGIT, TGF-beta, BTLA, MICA, NKG2A, KIR, CD160, Chop, and/or Xbp1. In addition or alternatively, the oligonucleotide, the antibody and/or the small molecule inhibits or stimulates an immune stimulatory factor such as 4-1BB, Ox40, KIR, GITR, CD27 and/or 2B4.

Furthermore, the present invention relates to a method of preventing and/or treating a disorder, where a Chop imbalance is involved comprising administering the oligonucleotide or the pharmaceutical composition of the present invention. In some embodiments, the disorder is for example an autoimmune disorder, an immune disorder, diabetes, artheriosclerosis, a nephrological disorder and/or cancer. In some embodiments, the oligonucleotide or the pharmaceutical composition of the present invention is for example administered locally or systemically.

All documents cited or referenced herein ("herein cited documents"), and all documents cited or referenced in herein cited documents, together with any manufacturer's instructions, descriptions, product specifications, and product sheets for any products mentioned herein or in any document incorporated by reference herein, are hereby incorporated herein by reference, and may be employed in the practice of the invention. More specifically, all referenced documents are incorporated by reference to the same extent as if each individual document was specifically and individually indicated to be incorporated by reference.

BRIEF DESCRIPTION OF DRAWINGS

FIG. 1 shows the mRNA sequence of human (h) Chop (SEQ ID No. 1; reference NM_001195053).

FIG. 2 depicts the distribution of hChop antisense oligonucleotide binding sites on the hChop mRNA of SEQ ID No. 1 as well as their modification(s) and length. hChop antisense oligonucleotides were aligned to the hChop mRNA sequence. The different grayscales indicate the different LNA modifications and symbols indicate the different length of the antisense oligonucleotides.

FIGS. 3A and 3B depict hChop mRNA knockdown efficacy of hChop antisense oligonucleotides in human cancer cell lines EFO-21 (ovarian cystadenocarcinoma) in a first screening round (FIG. 3A) and SKOV-3 (ovarian adenocarcinoma) in a first screening round (FIG. 3B). EFO-21 and SKOV-3 cells were treated for 3 days with 5 µM of the respective antisense oligonucleotide without transfection reagent. As negative control, cells were treated with S6, an antisense oligonucleotide having the sequence TCTATCGT-GATGTTTCT. Residual hChop mRNA expression relative to untreated cells is depicted. Expression values were normalized to expression of the housekeeping gene HPRT1.

FIGS. 4A and 4B depict hChop mRNA knockdown efficacy of hChop antisense oligonucleotides in human cancer cell lines EFO-21 (ovarian cystadenocarcinoma) in a second screening round (FIG. 4A) and SKOV-3 (ovarian adenocarcinoma) in a second screening round (FIG. 4B). EFO-21 and SKOV-3 cells were treated for 3 days with 5 µM of the respective antisense oligonucleotide without transfection reagent. As negative control, cells were treated with neg1, an antisense oligonucleotide having the sequence CGTT-TAGGCTATGTACTT (described in WO2014154843 A1). Residual hChop mRNA expression relative to untreated cells (EFO-21) or control antisense oligonucleotide treated cells (SKOV-3) is depicted. Expression values were normalized to expression of the housekeeping gene HPRT1.

FIG. 5 shows concentration-dependent hChop mRNA knockdown by selected hChop antisense oligonucleotides in EFO-21 cells which were A19001H (SEQ ID No.8), A19003H (SEQ ID No.4), A19018HM (SEQ ID No.2), A19020HM (SEQ ID No.3), A19027H (SEQ ID No.5), A19028H (SEQ ID No.6) and A19037H (SEQ ID No.7). EFO-21 cells were treated for 3 days with the indicated concentration of the respective antisense oligonucleotide. Residual hChop expression is depicted compared to untreated control cells. hChop mRNA expression values were normalized to expression of the housekeeping gene HPRT1. Concentration-dependent target knockdown was used for calculation of $IC_{50}$ values shown in Table 11.

FIG. 6 depicts knockdown of Chop mRNA in activated human CD8+ T cells in response to treatment with Chop antisense oligonucleotides. CD8+ T cells were activated with tetrameric CD2/CD3/CD28 antibody complexes for three days and treated with the Chop antisense oligonucleotide A19018HM (SEQ ID No. 2) or the negative control neg1 at a concentration of 5 µM. Residual hChop expression is depicted compared to untreated control cells. hChop mRNA expression values were normalized to expression of the housekeeping gene HPRT1.

FIGS. 7A and 7B depict an efficacy screen of human/mouse cross reactive Chop antisense oligonucleotides in murine cancer cell lines Renca (mouse renal adenocarcinoma) in a first screening round (see FIG. 7A) and 4T1 (tumor of the mammary gland) in a first screening round, respectively, (see FIG. 7B). Cells were treated for 3 days with 5 µM of the respective antisense oligonucleotide without transfection reagent. As negative control, cells were treated with S6, an antisense oligonucleotide having the sequence TCTATCGTGATGTTTCT. Residual-Chop mRNA expression relative to untreated cells is depicted. Expression values were normalized to expression of the housekeeping gene HPRT1.

FIGS. 8A and 8B depict an efficacy screen of human/mouse cross reactive Chop antisense oligonucleotides in murine cancer cell lines Renca (mouse renal adenocarcinoma) in a second screening round (see FIG. 8A) and 4T1 (tumor of the mammary gland) in a second screening round, respectively, (see FIG. 8B). Cells were treated for 3 days with 5 µM of the respective antisense oligonucleotide without transfection reagent. As negative control, cells were treated with neg1, an antisense oligonucleotide having the sequence CGTTTAGGCTATGTACTT (described in WO2014154843 A1). Residual-Chop mRNA expression relative to untreated cells is depicted. Expression values were normalized to expression of the housekeeping gene HPRT1.

FIG. 9 shows concentration-dependent Chop mRNA knockdown by selected-Chop antisense oligonucleotides in Renca cells which were A19018HM (SEQ ID No.2) and A19021HM (SEQ ID No.20). Renca cells were treated for 3 days with the indicated concentration of the respective antisense oligonucleotide. Residual-Chop expression is depicted compared to untreated control cells. Chop mRNA expression values were normalized to expression of the housekeeping gene HPRT1. Concentration-dependent target knockdown was used for calculation of $IC_{50}$ values shown in Table 16.

FIG. 10 depicts knockdown of Chop mRNA in murine myeloid derived suppressor cells (MDSC) using Chop antisense oligonucleotides of the present invention. Cells were treated for 3 days with 5 µM of A19018HM (SEQ ID No. 2) or the negative control neg1. Residual Chop mRNA expression relative to untreated cells is depicted. Expression values were normalized to expression of the housekeeping gene HPRT1.

FIG. 11 shows the introns of the pre-mRNA sequence of human (h) Chop (SEQ ID No. 48; reference ENST00000551116.5).

FIG. 12 depicts efficacy screening of intronic Chop antisense oligonucleotides in EFO-21 cells. In order to investigate the knockdown efficacy of the in silico designed intronic Chop antisense oligonucleotides, an efficacy screening round in the cancer cell line EFO-21 (human Ovarian Cystadenocarcinoma, DSMZ) was performed. Cells were treated with the respective antisense oligonucleotide at a concentration of 5 µM for three days without the addition of a transfection reagent. A19018HM (SEQ ID NO.2) was used as a reference Chop antisense oligonucleotide that binds to an exonic region of Chop RNA

DETAILED DESCRIPTION

Figure 3B:
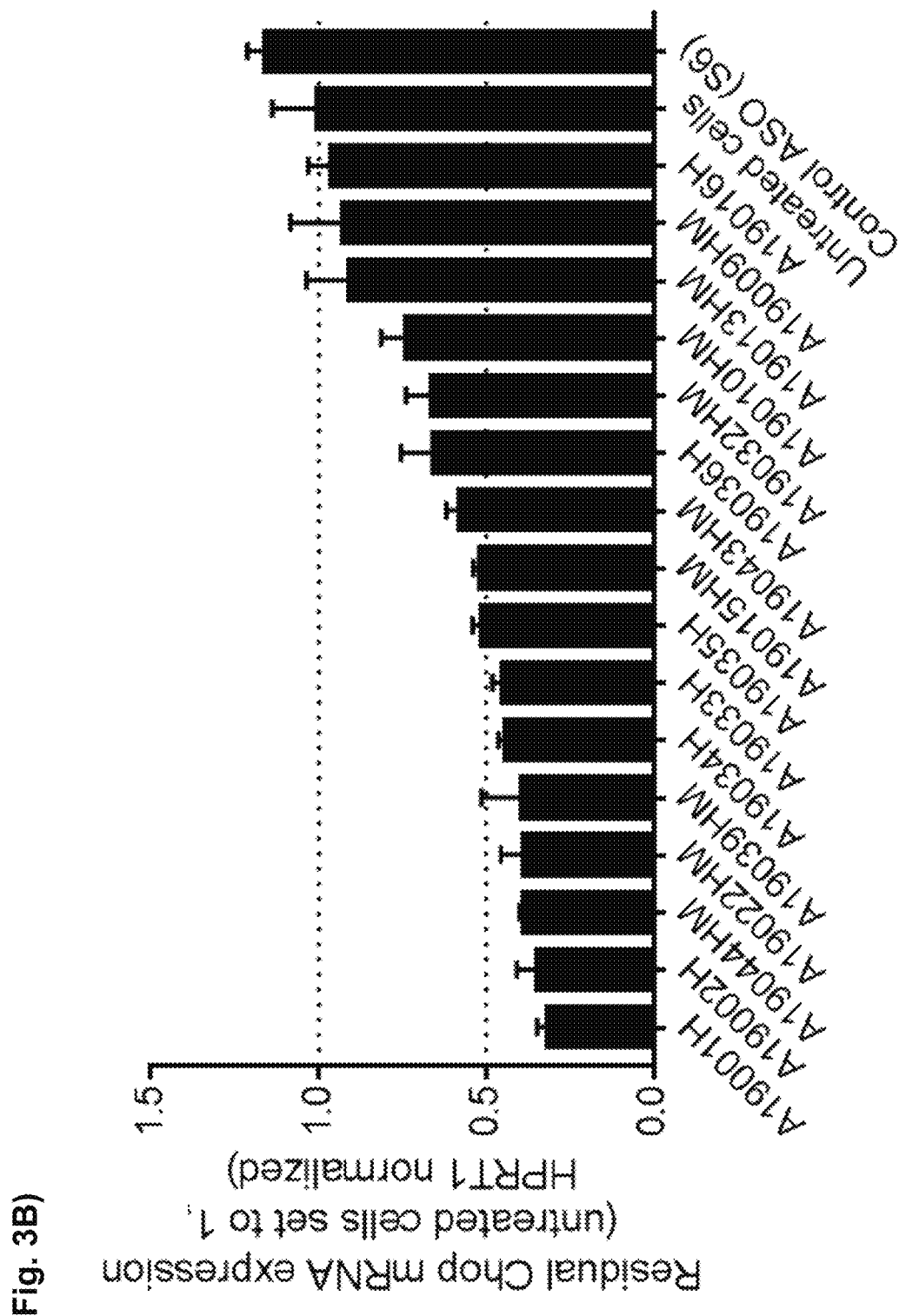

The present invention provides for the first time human and murine oligonucleotides which hybridize with mRNA and/or pre-mRNA sequences of C/EBP-homologous protein (Chop) and inhibit the expression and activity, respectively, of Chop. mRNA comprises only exons and untranslated regions (UTRs) of the Chop encoding nucleic acid sequence, whereas pre-mRNA comprises exons, introns and UTRs of the Chop encoding nucleic acid sequence. Thus, the oligonucleotides of the present invention represent an interesting and highly efficient tool for use in a method of preventing and/or treating disorders, where the Chop expression and activity, respectively, is increased comprising administering the oligonucleotides of the present invention.

In the following, the elements of the present invention will be described in more detail. These elements are listed with specific embodiments, however, it should be understood that they may be combined in any manner and in any number to create additional embodiments. The variously described examples and embodiments should not be construed to limit the present invention to only the explicitly described embodiments. This description should be understood to support and encompass embodiments which combine the explicitly described embodiments with any number of the disclosed elements. Furthermore, any permutations and combinations of all described elements in this application should be considered disclosed by the description of the present application unless the context indicates otherwise.

Throughout this specification and the claims, unless the context requires otherwise, the word "comprise", and variations such as "comprises" and "comprising", will be understood to imply the inclusion of a stated member, integer or step or group of members, integers or steps but not the exclusion of any other member, integer or step or group of members, integers or steps. The terms "a" and "an" and "the" and similar reference used in the context of describing the invention (especially in the context of the claims) are to be construed to cover both the singular and the plural, unless otherwise indicated herein or clearly contradicted by the context. Recitation of ranges of values herein is merely intended to serve as a shorthand method of referring individually to each separate value falling within the range. Unless otherwise indicated herein, each individual value is incorporated into the specification as if it were individually recited herein. All methods described herein can be performed in any suitable order unless otherwise indicated herein or otherwise clearly contradicted by context. The use of any and all examples, or exemplary language (e.g., "such as", "for example"), provided herein is intended merely to better illustrate the invention and does not pose a limitation on the scope of the invention otherwise claimed. No language in the specification should be construed as indicating any non-claimed element essential to the practice of the invention.

An oligonucleotide of the present invention is for example an antisense oligonucleotide (ASO) consisting of or comprising 10 to 25 nucleotides, 10 to 15 nucleotides, 15 to 20 nucleotides, 12 to 18 nucleotides, or 14 to 17 nucleotides. The oligonucleotides for example consist of or comprise 10, 11, 12, 13, 14, 15, 16, 17, 18, 19, 20, 21, 22, 23, 24 or 25 nucleotides. The oligonucleotides of the present invention comprise at least one nucleotide which is modified. The modified nucleotide is for example a bridged nucleotide such as a locked nucleic acid (LNA, e.g., 2',4'-LNA), cET, ENA, a 2'Fluoro modified nucleotide, a 2'O-Methyl modified nucleotide or a combination thereof. In some embodiments, the oligonucleotide of the present invention comprises nucleotides having the same or different modifications. In some embodiments the oligonucleotide of the present invention comprises a modified phosphate backbone, wherein the phosphate is for example a phosphorothioate.

The oligonucleotide of the present invention comprises the one or more modified nucleotide at the 3'- and/or 5'-end of the oligonucleotide and/or at any position within the oligonucleotide, wherein modified nucleotides follow in a row of 1, 2, 3, 4, 5, or 6 modified nucleotides, or a modified nucleotide is combined with one or more unmodified nucleotides. The following Tables 1 and 2 present embodiments of oligonucleotides comprising modified nucleotides for example LNA which are indicated by (+) and phosphorothioate (PTO) indicated by (*). The oligonucleotides consisting of or comprising the sequences of Table 1 or 2 may comprise any other modified nucleotide and/or any other combination of modified and unmodified nucleotides. Oligonucleotides of Table 1 hybridize with mRNA of human Chop:

TABLE 1

List of antisense oligonucleotides hybridizing with human Chop for example of SEQ ID No. 1; Neg1 and S6 are antisense oligonucleotides representing a negative control which is not hybridizing with Chop of SEQ ID No. 1. Some of these oligonucleotides do not only hybridize with human mRNA (H), but also with mouse and/or rat Chop mRNA (HM).

| Seq ID | Name | Antisense Sequence 5'-3' | Antisense Sequence 5'-3' with PTO (*) and LNA (+) |
|---|---|---|---|
| 2 | A19018HM | CTAGCTGTGCCACTTT | +C*+T*+A*G*C*T*G*T*G*C*C*A*C*+T*+T*+T |
| 3 | A19020HM | TTTCCTGCTTGAGCCG | +T*+T*+T*C*C*T*G*C*T*T*G*A*G*C*+C*+G |
| 4 | A19003H | ACATGATACGCTCAGT | +A*+C*+A*T*G*A*T*A*C*G*C*T*C*+A*+G*+T |
| 5 | A19027H | CAGATTCACCATTCGGT | +C*+A*+G*A*T*T*C*A*C*C*A*T*T*C*+G*+G*+T |
| 6 | A19028H | ATGCTTGGTGCAGATTC | +A*+T*+G*C*T*T*G*G*T*G*C*A*G*A*+T*+T*+C |
| 7 | A19037H | TCTATATACAAGCTGA | +T*+C*+T*A*T*A*T*A*C*A*A*G*C*+T*+G*+A |
| 8 | A19001H | TACGCTCAGTGCCTTAG | +T*+A*+C*G*C*T*C*A*G*T*G*C*C*T*+T*+A*+G |
| 9 | A19002H | TGATACGCTCAGTGCCT | +T*+G*+A*T*A*C*G*C*T*C*A*G*T*G*+C*+C*+T |
| 10 | A19031HM | GTTCATGCTTGGTGCAG | +G*+T*+T*C*A*T*G*C*T*T*G*G*T*G*+C*+A*+G |
| 11 | A19024HM | TCAGGCGCTCGATTT | +T*+C*+A*G*G*C*G*C*T*C*G*A*+T*+T*+T |
| 12 | A19030HM | TTCATGCTTGGTGCAG | +T*+T*+C*A*T*G*C*T*T*G*G*T*G*+C*+A*+G |
| 13 | A19017H | CCTTCATGCGCTGCTTT | +C*+C*+T*T*C*A*T*G*C*G*C*T*G*C*+T*+T*+T |
| 14 | A19022HM | CTCGATTTCCTGCTTG | +C*+T*+C*G*A*T*T*T*C*C*T*G*C*+T*+T*+G |
| 15 | A19044HM | GTTCATGCTTGGTGCA | +G*+T*+T*C*A*T*G*C*T*T*G*G*T*+G*+C*+A |
| 16 | A19033H | ACATCATTGGCACTAGT | +A*+C*+A*T*C*A*T*T*G*G*C*A*C*T*+A*+G*+T |
| 17 | A19015HM | CCACTCTGTTTCCGTTT | +C*+C*+A*C*T*C*T*G*T*T*T*C*C*G*+T*+T*+T |
| 18 | A19004H | AACATGATACGCTCAG | +A*+A*+C*A*T*G*A*T*A*C*G*C*T*+C*+A*+G |
| 19 | A19029H | TCATGCTTGGTGCAGAT | +T*+C*+A*T*G*C*T*T*G*G*T*G*C*A*+G*+A*+T |
| 20 | A19021HM | TCGATTTCCTGCTTG | +T*+C*+G*A*T*T*T*C*C*T*G*C*+T*+T*+G |
| 21 | A19035H | TATACAAGCTGAGACC | +T*+A*+T*A*C*A*A*G*C*T*G*A*G*+A*+C*+C |
| 22 | A19034H | GGTCACATCATTGGCAC | +G*+G*+T*C*A*C*A*T*C*A*T*T*G*G*+C*+A*+C |
| 23 | A19050HM | TTTACCTCCAGCCTCCT | +T*+T*+T*A*C*C*T*C*C*A*G*C*C*T*+C*+C*+T |
| 24 | A19032HM | GTTCATGCTTGGTGCA | +G*+T*+T*C*A*T*G*C*T*T*G*G*T*+G*+C*+A |
| 15 | A19043HM | GTTCATGCTTGGTGCA | +G*+T*+T*C*A*T*G*C*T*T*G*G*T*+G*+C*+A |
| 25 | A19019H | TTTCCTGCTTGAGCCGT | +T*+T*+T*C*C*T*G*C*T*T*G*A*G*C*+C*+G*+T |
| 26 | T19010HM | TCATACCAGGCTTCCAG | +T*+C*+A*T*A*C*C*A*G*G*C*T*T*C*+C*+A*+G |
| 27 | A19036H | TATATACAAGCTGAGAC | +T*+A*+T*A*T*A*C*A*A*G*C*T*G*A*+G*+A*+C |
| 28 | A19009HM | CATACCAGGCTTCCAGC | +C*+A*+T*A*C*C*A*G*G*C*T*T*C*C*+A*+G*+C |
| 29 | A19007H | TGGCAAGCTGGTCTGAT | +T*G*+G*C*A*A*G*C*T*G*G*T*C*T*+G*+A*+T |
| 30 | A19048HM | ATCCAGGCTGCTCTCTT | +A*+T*+C*C*A*G*G*C*T*G*C*T*C*T*+C*+T*+T |
| 31 | A19016H | CATGCGCTGCTTTCCAG | +C*+A*+T*G*C*G*C*T*G*C*T*T*T*C*+C*+A*+G |
| 32 | A19014HM | CACTCTGTTTCCGTTTC | +C*+A*+C*T*C*T*G*T*T*T*C*C*G*T*+T*+T*+C |
| 33 | A19023HM | CAGGCGCTCGATTTC | +C*+A*+G*G*C*G*C*T*C*G*A*T*+T*+T*+C |
| 34 | A19013HM | CTCTGACTGGAATCTGG | +C*+T*+C*T*G*A*C*T*G*G*A*A*T*C*+T*+G*+G |

TABLE 1-continued

List of antisense oligonucleotides hybridizing with human Chop for example of
SEQ ID No. 1; Neg1 and S6 are antisense oligonucleotides representing a negative control
which is not hybridizing with Chop of SEQ ID No. 1. Some of these oligonucleotides do not
only hybridize with human mRNA (H), but also with mouse and/or rat Chop mRNA (HM).

| Seq ID | Name | Antisense Sequence 5'-3' | Antisense Sequence 5'-3' with PTO (*) and LNA (+) |
|---|---|---|---|
| 35 | A19039HM | GCTCTGTCGCTGCCACC | +G*+C*+T*C*T*G*T*C*G*C*T*G*C*C*+A*C*+C |
| 36 | A19042HM | TCCTCATACCAGGCT | +T*+C*C*T*C*A*T*A*C*C*A*G*G*+C*+T |
| 36 | A19041HM | TCCTCATACCAGGCT | +T*+C*+C*T*C*A*T*A*C*C*A*G*+G*+C*+T |
| 35 | A19038HM | GCTCTGTCGCTGCCACC | +G*+C*+T*C*T*G*T*C*G*C*T*G*C*C*+A*+C*+C |
| 37 | A19005HM | GCTCTGTCGCTGCCACC | +G*+C*+T*C*T*G*T*C*G*C*T*G*C*C*A*+C*+C |
| 30 | A19049HM | ATCCAGGCTGCTCTCTT | +A*+T*C*C*A*G*G*C*T*G*C*T*C*T*C*+T*+T |
| 38 | A19047HM | CCAGGCTGCTCTCTTGT | +C*+C*+A*G*G*C*T*G*C*T*C*T*C*T*T*+G*+T |
| 39 | A19025HM | TGGTCAGGCGCTCGA | +T*+G*+G*T*C*A*G*G*C*G*C*T*+C*+G*+A |
| 40 | A19026H | CGAGTCGCCTCTACTTC | +C*+G*A*G*T*C*G*C*C*T*C*T*A*C*+T*+T*+C |
| 41 | A19011H | GGTCCTCATACCAGGCT | +G*+G*+T*C*C*T*C*A*T*A*C*C*A*G*+G*+C*+T |
| 36 | A19040HM | TCCTCATACCAGGCT | +T*+C*+C*T*C*A*T*A*C*C*A*G*G*+C*+T |
| 42 | A19045HM | CAGGCTGCTCTCTTGT | +C*+A*+G*G*C*T*G*C*T*C*T*C*T*T*+G*+T |
| 42 | A19046HM | CAGGCTGCTCTCTTGT | +C*+A*G*G*C*T*G*C*T*C*T*C*T*T*+G*+T |
| 43 | A19008H | TCTGCAGTTGGATCAGT | +T*+C*+T*G*C*A*G*T*T*G*G*A*T*C*A*+G*+T |
| 44 | A19012H | GTGACCTCTGCTGGTT | +G*T*+G*A*C*C*T*C*T*G*C*T*G*G*+T*+T |
| 45 | A19006HM | ACTCTCTCCTCAGGTTC | +A*+C*T*C*T*C*T*C*C*T*C*A*G*G*+T*T*+C |
| 46 | Neg1 |  | +C*+G*+T*T*T*A*G*G*C*T*A*T*G*T*A*+C*+T*+T |
| 47 | S6 |  | +T*+C*+T*A*T*C*G*T*G*A*T*G*T*T*+T*+C*+T |

Oligonucleotides of Table 2 hybridize with intronic regions of the pre-mRNA of human Chop:

TABLE 2

List of antisense oligonucleotides hybridizing with human Chop for example of
SEQ ID No. 48; Neg1 is an antisense oligonucleotides representing a negative control
which is not hybridizing with Chop of SEQ ID No. 48. Some of these oligonucleotides do
not only hybridize with introns of human pre-mRNA (HI), but also with introns of mouse
and/or rat Chop pre-mRNA (HM).

| Seq Id No. | Name | Antisense sequence 5'-3' | Antisense sequence 5'-3' with PTO and LNA (+) |
|---|---|---|---|
| 42 | A19045HM | CAGGCTGCTCTCTTGT | +C*+A*+G*G*C*T*G*C*T*C*T*C*T*+T*+G*+T |
| 42 | A19046HM | CAGGCTGCTCTCTTGT | +C*+A*G*G*C*T*G*C*T*C*T*C*T*T*+G*+T |
| 38 | A19047HM | CCAGGCTGCTCTCTTGT | +C*+C*+A*G*G*C*T*G*C*T*C*T*C*T*T*+G*+T |
| 30 | A19048HM | ATCCAGGCTGCTCTCTT | +A*+T*+C*C*A*G*G*C*T*G*C*T*C*T*C*+T*+T |
| 30 | A19049HM | ATCCAGGCTGCTCTCTT | +A*+T*C*C*A*G*G*C*T*G*C*T*C*T*C*+T*+T |
| 23 | A19050HM | TTTACCTCCAGCCTCCT | +T*+T*+T*A*C*C*T*C*C*A*G*C*C*T*C*+C*+T |
| 49 | A19051HI | ATCCTAAAGAGCGGACG | +A*+T*+C*C*T*A*A*A*G*A*G*C*G*G*+A*+C*+G |
| 50 | A19052HI | GTGAGGCCGATCCTAAA | +G*+T*+G*A*G*G*C*C*G*A*T*C*C*T*+A*+A*+A |
| 51 | A19053HI | AGTGAGGCCGATCCTAA | +A*+G*+T*G*A*G*G*C*C*G*A*T*C*C*+T*+A*+A |

TABLE 2-continued

List of antisense oligonucleotides hybridizing with human Chop for example of
SEQ ID No. 48; Neg1 is an antisense oligonucleotides representing a negative control
which is not hybridizing with Chop of SEQ ID No. 48. Some of these oligonucleotides do
not only hybridize with introns of human pre-mRNA (HI), but also with introns of mouse
and/or rat Chop pre-mRNA (HM).

| Seq Id No. | Name | Antisense sequence 5'-3' | Antisense sequence 5'-3' with PTO and LNA (+) |
|---|---|---|---|
| 52 | A19054HI | ATTCCTCTCTCGGACGG | +A*+T*+T*C*C*T*C*T*C*T*C*G*G*A*C*+G*+G |
| 53 | A19055HI | GTCGTCCGAAGCAATAG | +G*+T*+C*G*T*C*C*G*A*A*G*C*A*A*+T*+A*+G |
| 54 | A19056HI | CCGTCGTCCGAAGCAAT | +C*+C*+G*T*C*G*T*C*C*G*A*A*G*C*+A*+A*+T |
| 55 | A19057HI | GCCGTCGTCCGAAGCAA | +G*+C*+C*G*T*C*G*T*C*C*G*A*A*G*+C*+A*+A |
| 56 | A19058HI | TAACGATGAGGCCTGAA | +T*A*+A*C*G*A*T*G*A*G*G*C*C*T*+G*A*+A |
| 57 | A19059HI | GGACAGGCCTAACGATG | +G*+G*+A*C*A*G*G*C*C*T*A*A*C*G*+A*+T*+G |
| 58 | A19060HI | GACAGGCCTAACGATG | +G*+A*+C*A*G*G*C*C*T*A*A*C*G*+A*+T*+G |
| 59 | A19061HI | AACGGCCTGAGCGATGG | +A*+A*+C*G*G*C*C*T*G*A*G*C*G*A*+T*+G*+G |
| 60 | A19062HI | GGAAACGGCCTGAGCGA | +G*+G*+A*A*A*C*G*G*C*C*T*G*A*G*+C*+G*+A |
| 61 | A19063HI | GAAGCGGCGGAAACGGC | +G*+A*+A*G*C*G*G*C*G*G*A*A*A*C*+G*+G*+C |
| 62 | A19064HI | AGAGACCTCTACGGCAA | +A*+G*A*G*A*C*C*T*C*T*A*C*G*G*C*+A*+A |
| 63 | A19065HI | GGCCTCCTACACTTAAG | +G*G*+C*C*+T*C*C*T*A*C*A*C*T*T*A*+A*+G |
| 64 | A19066HI | TGACCACCTGATGTAAC | +T*+G*+A*C*C*A*C*C*T*G*A*T*G*T*+A*+A*+C |
| 65 | A19067HI | TAAGGTAATTCCTGACC | +T*+A*+A*G*G*T*A*A*T*T*C*C*T*G*+A*+C*+C |
| 66 | A19068HI | CCTGCAATCCAAAGTAC | +C*+C*+T*G*C*A*A*T*C*C*A*A*A*G*+T*+A*+C |
| 67 | A19069HI | TTGTGATCCATCGCTTC | +T*+T*+G*T*G*A*T*C*C*A*T*C*G*C*+T*+T*+C |
| 68 | A19070HI | CCTTGTGATCCATCGCT | +C*+C*+T*T*G*T*G*A*T*C*C*A*T*C*+G*+C*+T |
| 69 | A19071HI | TACTGTCCTGCCGTTTA | +T*+A*+C*T*G*T*C*C*T*G*C*C*G*T*+T*+T*+A |
| 70 | A19072HI | AAGAGTCACGCTAGAGA | +A*+A*+G*A*G*T*C*A*C*G*C*T*A*G*+A*+G*+A |
| 46 | neg1 |  | +C*+G*+T*T*T*A*G*G*C*T*A*T*G*T*A*+C*+T*+T |

The oligonucleotides of the present invention hybridize for example with mRNA of human Chop of SEQ ID No. 1 and/or introns of the pre-mRNA of human Chop of SEQ ID No. 48. Such oligonucleotides are called Chop antisense oligonucleotides. In some embodiments, the oligonucleotides hybridize within a hybridizing active area which is one or more region(s) on the Chop mRNA, e.g., of SEQ ID No.1 and/or the Chop pre-mRNA, e.g., of SEQ ID No.48, where hybridization with an oligonucleotide highly likely results in a potent knockdown of the Chop expression. In the present invention surprisingly several hybridizing active areas were identified for example selected from hybridizing active areas for example selected from position 0 or 1 to 60, position 695 to 755, position 725 to 785, position 800 to 860, and/or position 970 to 1030 (including the terminal figures of the ranges) of Chop mRNA for example of SEQ ID No. 1. Examples of antisense oligonucleotides hybridizing within the above mentioned positions of Chop mRNA for example of SEQ ID No. 1 are shown in the following Tables 3 to 7 and examples of antisense oligonucleotides hybridizing within the above mentioned positions of Chop pre-mRNA for example of SEQ ID No. 48 are shown in the following Tables 8 to 21:

TABLE 3

Nucleotide position 0 to 60 of Chop mRNA of SEQ ID No. 1

| Binding site on hChop mRNA (Position of the first nucleotide) | SEQ ID No./ASO Name |
|---|---|
| 19 | 8/A19001H |
| 22 | 9/A19002H |
| 26 | 4/A19003H |
| 27 | 18/A19004H |

TABLE 4

Nucleotide position 695 to 755 of Chop mRNA of SEQ ID No. 1

| Binding site on hChop mRNA (Position of the first nucleotide) | SEQ ID No./ASO Name |
|---|---|
| 725 | 2/A19018HM |

TABLE 5

Nucleotide position 725 to 785 of Chop mRNA of SEQ ID No. 1

| Binding site on hChop mRNA (Position of the first nucleotide) | SEQ ID No./ASO Name |
|---|---|
| 754 | 25/A19019H |
| 755 | 3/A19020HM |
| 760 | 20/A19021HM |
| 760 | 14/A19022HM |
| 767 | 33/A19023HM |
| 768 | 11/A19024HM |

TABLE 6

Nucleotide position 800 to 860 of Chop mRNA of SEQ ID No. 1

| Binding site on hChop mRNA (Position of the first nucleotide) | SEQ ID No. Name |
|---|---|
| 819 | 5/A19027H |
| 829 | 6/A19028H |
| 831 | 19/A19029H |
| 833 | 12/A19030HM |
| 833 | 10/A19031HM |
| 834 | 24/A19032HM |

TABLE 7

Nucleotide position 970 to 1030 of Chop mRNA of SEQ ID No. 1

| Binding site on hChop mRNA (Position of the first nucleotide) | SEQ ID No./ASO Name |
|---|---|
| 992 | 21/A19035H |
| 993 | 27/A19036H |
| 996 | 7/A19037H |

TABLE 8

Nucleotide position 29 to 89 of Chop pre-mRNA of SEQ ID No. 48

| Binding site on hChop pre-mRNA (Position of the first nucleotide) | SEQ ID No./ASO Name |
|---|---|
| 54 | 49/A19051HI |
| 63 | 50/A19052HI |
| 64 | 51/A19053HI |

TABLE 9

Nucleotide position 90 to 132 of Chop pre-mRNA of SEQ ID No. 48

| Binding site on hChop pre-mRNA (Position of the first nucleotide) | SEQ ID No./ASO Name |
|---|---|
| 102 | 52/A19054HI |

TABLE 10

Nucleotide position 130 to 190 of Chop pre-mRNA of SEQ ID No. 48 (e.g., intron 1)

| Binding site on hChop pre-mRNA (Position of the first nucleotide) | SEQ ID No./ASO Name |
|---|---|
| 158 | 53/A19055HI |
| 160 | 54/A19056HI |
| 161 | 55/A19057HI |

TABLE 11

Nucleotide position 256 to 316 of Chop pre-mRNA of SEQ ID No. 48 (e.g., intron 1)

| Binding site on hChop pre-mRNA (Position of the first nucleotide) | SEQ ID No./ASO Name |
|---|---|
| 282 | 56/A19058HI |
| 291 | 57/A19059HI |
| 291 | 58/A19060HI |

TABLE 12

Nucleotide position 331 to 391 of Chop pre-mRNA of SEQ ID No. 48 (e.g., intron 1)

| Binding site on hChop pre-mRNA (Position of the first nucleotide) | SEQ ID No./ASO Name |
|---|---|
| 356 | 59/A19061HI |
| 359 | 60/A19062HI |
| 367 | 61/A19063HI |

TABLE 13

Nucleotide position 534 to 576 of Chop pre-mRNA of SEQ ID No. 48 (e.g., intron 1)

| Binding site on hChop pre-mRNA (Position of the first nucleotide) | SEQ ID No./ASO Name |
|---|---|
| 564 | 62/A19064HI |

TABLE 14

Nucleotide position 577 to 600 of Chop pre-mRNA of SEQ ID No. 48 (e.g., intron 1)

| Binding site on hChop pre-mRNA (Position of the first nucleotide) | SEQ ID No./ASO Name |
|---|---|
| 592 | 42/A19045HM |
| 592 | 42/A19046HM |
| 592 | 38/A19047HM |
| 594 | 30/A19048HM |
| 594 | 30/A19049HM |

TABLE 15

Nucleotide position 601 to 643 of Chop pre-mRNA of SEQ ID No. 48 (e.g., intron 1)

| Binding site on hChop pre-mRNA (Position of the first nucleotide) | SEQ ID No./ASO Name |
|---|---|
| 613 | 63/A19065HI |

TABLE 16

Nucleotide position 1108 to 1168 of Chop pre-mRNA of SEQ ID No. 48 (e.g., intron 1)

| Binding site on hChop pre-mRNA (Position of the first nucleotide) | SEQ ID No./ASO Name |
|---|---|
| 1132 | 64/A19066HI |
| 1144 | 65/A19067HI |

TABLE 17

Nucleotide position 1739 to 1799 of Chop pre-mRNA of SEQ ID No. 48 (e.g., intron 1)

| Binding site on hChop pre-mRNA (Position of the first nucleotide) | SEQ ID No./ASO Name |
|---|---|
| 1769 | 66/A19068HI |

TABLE 18

Nucleotide position 2241 to 2301 of Chop pre-mRNA of SEQ ID No. 48 (e.g., intron 1)

| Binding site on hChop pre-mRNA (Position of the first nucleotide) | SEQ ID No./ASO Name |
|---|---|
| 2271 | 23/A19050HM |

TABLE 19

Nucleotide position 2312 to 2372 of Chop pre-mRNA of SEQ ID No. 48 (e.g., intron 1)

| Binding site on hChop pre-mRNA (Position of the first nucleotide) | SEQ ID No./ASO Name |
|---|---|
| 2341 | 67/A19069HI |
| 2343 | 68/A19070HI |

TABLE 20

Nucleotide position 17 to 47 of Chop pre-mRNA of SEQ ID No. 48 (e.g., intron 2)

| Binding site on hChop pre-mRNA (Position of the first nucleotide) | SEQ ID No./ASO Name |
|---|---|
| 32 | 69/A19071HI |

TABLE 21

Nucleotide position 61 to 91 of Chop pre-mRNA of SEQ ID No. 48 (e.g., intron 2)

| Binding site on hChop pre-mRNA (Position of the first nucleotide) | SEQ ID No./ASO Name |
|---|---|
| 76 | 70/A19072HI |

In Tables 3 to 21 "ASO" is the abbreviation for "antisense oligonucleotide" and the sequences and LNA patterns of the ASOs are specified in Tables 1 and 2, respectively.

In some embodiments, the oligonucleotide of the present invention inhibits for example at least about 50%, 55%, 60%, 65%, 70%, 75%, 80%, 85%, 90%, 92%, 94%, 95%, 96%, 97%, 98%, 99% or 100% of Chop such as the, e.g., human, rat or murine, Chop expression. Thus, the oligonucleotides of the present invention are for example immunosuppression-reverting oligonucleotides which inhibit and revert immunosuppression, respectively, for example in a cell, tissue, organ, or a subject. The oligonucleotide of the present invention inhibits the expression of Chop at a nanomolar or micromolar concentration for example in a concentration of 0.1, 1, 2, 3, 4, 5, 6, 7, 8, 9, 10, 15, 20, 25, 30, 35, 40, 45, 50, 55, 60, 65, 70, 75, 80, 85, 90, 95, 100, 150, 200, 250, 300, 350, 400, 450, 500, 550, 600, 650, 700, 750, 800, 850, 900 or 950 nM, or 1, 10 or 100 µM.

In some embodiments, the oligonucleotide of the present invention is used in a concentration of 1, 3, 5, 9, 10, 15, 27, 30, 40, 50, 75, 82, 100, 250, 300, 500, or 740 nM, or 1, 2.2, 3, 5, 6.6 or 10 µM.

In some embodiments the present invention refers to a pharmaceutical composition comprising an oligonucleotide of the present invention and a pharmaceutically acceptable carrier, excipient and/or dilutant. In some embodiments, the pharmaceutical composition further comprises a chemotherapeutic, another disease specific active agent such as insulin, angiotensin-converting enzyme inhibitor, angiotensin receptor blocker, another oligonucleotide, an antibody, a HERA fusion protein, a ligand trap, a Fab fragment, a nanobody, a BiTe and/or a small molecule which is for example effective in tumor treatment, treatment of diabetes and its side effects, treatment of obesity, treatment of nephrological diseases, and/or treatment of artheriosclerosis.

In some embodiments, the oligonucleotide or the pharmaceutical composition of the present invention is for use in a method of preventing and/or treating a disorder comprising administering the oligonucleotide or the pharmaceutical composition to a subject. In some embodiments, the method of preventing and/or treating a disorder is combined with radiotherapy. The radiotherapy may be further combined with a chemotherapy (e.g., platinum, gemcitabine). The disorder is for example characterized by an Chop imbalance, i.e., the Chop level is increased in comparison to the level in a normal, healthy cell, tissue, organ or subject. The Chop level is for example increased by an increased Chop expression and activity, respectively. The Chop level can be measured by any standard method such as immunohistochemistry, western blot, quantitative real time PCR or QuantiGene assay known to a person skilled in the art.

An oligonucleotide or a pharmaceutical composition of the present invention is administered locally or systemically for example orally, sublingually, nasally, subcutaneously, intravenously, intraperitoneally, intramuscularly, intratumoral, intrathecal, transdermal, and/or rectal. Alternatively or in combination ex vivo treated immune cells are administered. The oligonucleotide is administered alone or in combination with another antisense oligonucleotide of the present invention and optionally in combination with another compound such as another oligonucleotide, an antibody, a HERA fusion protein, a ligand trap, a Fab fragment, a nanobody, a BiTe, a small molecule and/or a chemotherapeutic (e.g., platinum, gemcitabine) and/or another disease specific agent such as insulin, angiotension-converting enzyme inhibitor, and/or angiotensin receptor blocker. In some embodiments, the other oligonucleotide (i.e., not being part of the present invention), the antibody, a HERA fusion protein, a ligand trap, a Fab fragment, a nanobody, a BiTe, and/or the small molecule are effective in preventing and/or treating an autoimmune disorder, an immune disorder, diabetes, artheriosclerosis, a nephrological disorder and/or cancer. An oligonucleotide or a pharmaceutical composition of the present invention is used for example in a method of preventing and/or treating a solid tumor or a hematologic tumor comprising administering the oligonucleotide or the pharmaceutical composition of the present invention to a subject. Examples of cancers preventable and/or treatable by use of the oligonucleotide or pharmaceutical composition of the present invention are breast cancer, lung cancer, malignant melanoma, lymphoma, skin cancer, bone cancer, prostate cancer, liver cancer, brain cancer, cancer of the larynx, gall bladder, pancreas, testicular, rectum, parathyroid, thyroid, adrenal, neural tissue, head and neck, colon, stomach, bronchi, kidneys, basal cell carcinoma, squamous cell carcinoma, metastatic skin carcinoma, osteo sarcoma, Ewing's sarcoma, reticulum cell sarcoma, liposarcoma, myeloma, giant cell tumor, small-cell lung tumor, islet cell tumor, primary brain tumor, meningioma, acute and chronic lymphocytic and granulocytic tumors, acute and chronic myeloid leukemia, hairy-cell tumor, adenoma, hyperplasia, medullary carcinoma, intestinal ganglioneuromas, Wilm's tumor, seminoma, ovarian tumor, leiomyomater tumor, cervical dysplasia, retinoblastoma, soft tissue sarcoma, malignant carcinoid, topical skin lesion, rhabdomyosarcoma, Kaposi's sarcoma, osteogenic sarcoma, malignant hypercalcemia, renal cell tumor, polycythermia vera, adenocarcinoma, anaplastic astrocytoma, glioblastoma multiforma, leukemia, or epidermoid carcinoma.

Further examples of diseases preventable and/or treatable by use of the oligonucleotide or pharmaceutical composition of the present invention other than cancer are for example diabetes, insulin resistance, type 2 diabetes mellitus, diabetic nephropathy, obesity and artheriosclerosis.

In some embodiments two or more oligonucleotides of the present invention are administered together, at the same time point for example in a pharmaceutical composition or separately, or on staggered intervals. In other embodiments, one or more oligonucleotides of the present invention are administered together with another compound such as another oligonucleotide (i.e., not being part of the present invention), an antibody, a HERA fusion protein, a ligand trap, a Fab fragment, a nanobody, a BiTe, a small molecule and/or a chemotherapeutic, at the same time point for example in a pharmaceutical composition or separately, or on staggered intervals. In some embodiments of these combinations, the antisense oligonucleotide inhibits the expression and activity, respectively, of an immune suppressive factor and the other oligonucleotide (i.e., not being part of the present invention), the antibody, a HERA fusion protein, a ligand trap, a Fab fragment, a nanobody, a BiTe and/or small molecule inhibits (antagonist) or stimulates (agonist) the same and/or another immune suppressive factor and/or an immune stimulatory factor. The immune suppressive factor is for example selected from the group consisting of IDOL IDO2, CTLA-4, PD-1, PD-L1, LAG-3, VISTA, A2AR, CD39, CD73, STAT3, TDO2, TIM-3, TIGIT, TGF-beta, BTLA, MICA, NKG2A, KIR, CD160, Chop, Xbp1 and a combination thereof. The immune stimulatory factor is for example selected from the group consisting of 4-1BB, Ox40, KIR, GITR, CD27, 2B4 and a combination thereof.

The immune suppressive factor is a factor whose expression and/or activity is for example increased in a cell, tissue, organ or subject. The immune stimulatory factor is a factor whose level is increased or decreased in a cell, tissue, organ or subject depending on the cell, tissue, organ or subject and its individual conditions.

An antibody in combination with the oligonucleotide or the pharmaceutical composition of the present invention is for example an anti-PD-1 antibody, an anti-PD-L1 antibody, or a bispecific antibody. A small molecule in combination with the oligonucleotide or the pharmaceutical composition of the present invention are for example NLG919, Indoximod, or Epacadostat.

A subject of the present invention is for example a mammalian, a bird or a fish.

EXAMPLES

The following examples illustrate different embodiments of the present invention, but the invention is not limited to these examples. The following experiments are performed on cells endogenously expressing Chop, i.e., the cells do not represent an artificial system comprising transfected reporter constructs. Such artificial systems generally show a higher degree of inhibition and lower $IC_{50}$ values than endogenous systems which are closer to therapeutically relevant in vivo systems. Further, in the following experiments no transfecting agent is used, i.e., gymnotic delivery is performed. Transfecting agents are known to increase the activity of an oligonucleotide which influences the $IC_{50}$ value (see for example Zhang et al., Gene Therapy, 2011, 18, 326-333; Stanton et al., Nucleic Acid Therapeutics, Vol. 22, No. 5, 2012). As artificial systems using a transfecting agent are hard or impossible to translate into therapeutic approaches and no transfection formulation has been approved so far for oligonucleotides, the following experiments are performed without any transfecting agent.

Example 1: Efficacy Screen of Chop Antisense Oligonucleotides in Human Cancer Cell Lines (First Screening Round)

In order to investigate the knockdown efficacy of the in silico designed Chop antisense oligonucleotides of Table 1, two efficacy screening rounds were performed in the cancer cell lines EFO-21 (human Ovarian Cystadenocarcinoma, DSMZ) and SKOV-3 (human Ovary Adenocarcinoma, ATCC). Therefore, cells were treated with the respective antisense oligonucleotide at a concentration of 5 µM for three days without the addition of a transfection reagent. Cells were lyzed after the three days treatment period, Chop and HPRT1 mRNA expression was analyzed using the QuantiGene Singleplex assay (ThermoFisher) and the Chop expression values were normalized to HPRT1 values. The results for the first screening round of antisense oligonucleotide are shown in FIGS. 3A and 3B as well as in the following Tables 22 and 23, wherein Chop expression has been calculated. As depicted in FIG. 3A) and Table 22, treatment of EFO-21 cells with the antisense oligonucleotides A19001H (SEQ ID NO.8), A19002H (SEQ ID NO.9), A19015HM (SEQ ID NO.17), A19022HM (SEQ ID NO.14), A19033H (SEQ ID NO.16), A19034H (SEQ ID NO.22), A19035H (SEQ ID NO.21) and A19044HM (SEQ ID NO.15) resulted in a residual Chop mRNA expression of <0.3 compared to untreated cells. The control antisense oligonucleotide S6 showed only a minimal effect on the Chop mRNA expression in this experiment. Selected antisense oligonucleotides were furthermore screened in SKOV-3 cells with regard to their Chop knockdown efficacy. As shown in FIG. 3B) and Table 23, treatment with the antisense oligonucleotides A19001H, A19002H, A19022HM, A19033H, A19034H, A19039HM (SEQ ID NO.35) and A19044HM resulted in a residual Chop mRNA expression of <0.5, whereas the control antisense oligonucleotide S6 had no effect.

TABLE 22

List of the mean Chop mRNA expression values in antisense oligonucleotide (ASO)-treated (first screening round) EFO-21 cells compared to untreated cells. Expression values are normalized to HPRT1.

| ASO | Residual Chop expression (compared to untreated cells) |
|---|---|
| A19001H | 0.22 |
| A19002H | 0.24 |
| A19022HM | 0.26 |
| A19044HM | 0.26 |
| A19033H | 0.26 |
| A19015HM | 0.27 |
| A19035H | 0.28 |
| A19034H | 0.28 |
| A19032HM | 0.30 |
| A19043HM | 0.30 |
| A19010HM | 0.31 |
| A19036H | 0.33 |
| A19009HM | 0.33 |
| A19016H | 0.42 |
| A19013HM | 0.45 |
| A19039HM | 0.51 |
| A19042HM | 0.53 |
| A19041HM | 0.55 |
| A19038HM | 0.55 |
| A19005HM | 0.56 |
| A19011H | 0.63 |
| A19040HM | 0.64 |
| Control ASO (S6) | 0.87 |
| Untreated cells | 1.00 |

TABLE 23

List of the mean Chop mRNA expression values in antisense oligonucleotide-treated (first screening round) SKOV-3 cells compared to untreated cells. Expression values are normalized to HPRT1.

| ASO | Residual Chop expression (compared to untreated cells) |
|---|---|
| A19001H | 0.32 |
| A19002H | 0.35 |
| A19044HM | 0.39 |
| A19022HM | 0.39 |
| A19039HM | 0.39 |
| A19034H | 0.44 |
| A19033H | 0.45 |
| A19035H | 0.51 |
| A19015HM | 0.51 |
| A19043HM | 0.58 |
| A19036H | 0.66 |
| A19032HM | 0.66 |
| A19010HM | 0.73 |
| A19013HM | 0.91 |
| A19009HM | 0.93 |
| A19016H | 0.96 |
| Untreated cells | 1.00 |
| Control ASO (S6) | 1.16 |

Example 2: Efficacy Screen of Chop Antisense Oligonucleotides in Human Cancer Cell Lines (Second Screening Round)

Figure 4B:
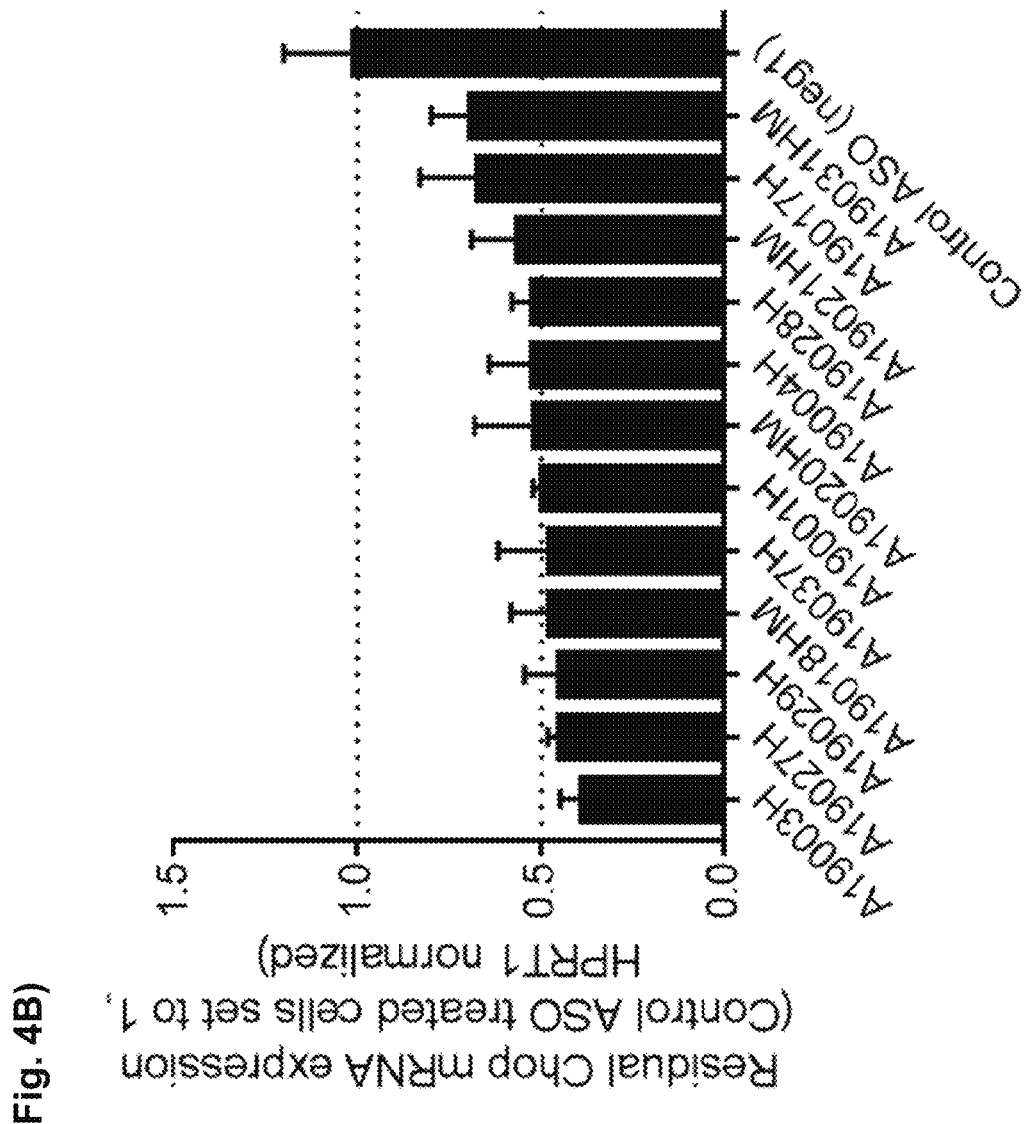

The results of the second screening round are shown in FIGS. 4A and 4B as well as in Tables 24 and 25. As depicted in FIG. 4A) and Table 24, treatment of EFO-21 cells with the antisense oligonucleotides A19001H (SEQ ID NO.8), A19018HM (SEQ ID NO.2), A19020HM (SEQ ID NO.3), A19027H (SEQ ID NO.5), A19028H (SEQ ID NO.6) and A19037H(SEQ ID NO.7) resulted in a residual Chop mRNA expression of <0.3 compared to untreated cells. The control antisense oligonucleotide neg1 showed a moderate negative effect on the Chop mRNA expression in this particular experiment which has not been observed in further experiments. Selected antisense oligonucleotides were furthermore screened in SKOV-3 cells with regard to their Chop knockdown efficacy. As shown in FIG. 4B) and Table 25, treatment with the antisense oligonucleotides A19001H (SEQ ID NO.8), A19003H (SEQ ID NO.4), A19018HM (SEQ ID NO.2), A19027H (SEQ ID NO.5), A19029H (SEQ ID NO.19) and A19037H (SEQ ID NO.7) resulted in a residual Chop mRNA expression of <0.5 compared to control antisense oligonucleotide (neg1) treated cells.

TABLE 24

List of the mean Chop mRNA expression values in antisense oligonucleotide-treated (second screening round) EFO-21 cells compared to untreated cells. Expression values are normalized to HPRT1.

| ASO | Residual Chop expression (compared to untreated cells) |
|---|---|
| A19037H | 0.19 |
| A19027H | 0.20 |
| A19028H | 0.21 |
| A19020HM | 0.29 |
| A19018HM | 0.30 |
| A19001H | 0.30 |
| A19003H | 0.31 |
| A19031HM | 0.33 |
| A19024HM | 0.34 |
| A19030HM | 0.34 |
| A19017H | 0.35 |
| A19004H | 0.37 |
| A19029H | 0.37 |
| A19021HM | 0.37 |
| A19050HM | 0.40 |
| A19019H | 0.41 |
| A19007H | 0.53 |
| A19048HM | 0.56 |
| A19014HM | 0.57 |
| A19023HM | 0.57 |
| Control ASO (neg1) | 0.58 |
| A19049HM | 0.78 |
| A19047HM | 0.82 |
| A19025HM | 0.83 |

TABLE 24-continued

List of the mean Chop mRNA expression values in antisense oligonucleotide-treated (second screening round) EFO-21 cells compared to untreated cells. Expression values are normalized to HPRT1.

| ASO | Residual Chop expression (compared to untreated cells) |
| --- | --- |
| A19026H | 0.84 |
| A19045HM | 0.88 |
| A19046HM | 0.98 |
| A19008H | 1.00 |
| Untreated cells | 1.00 |
| A19012H | 1.06 |
| A19006HM | 1.07 |

TABLE 25

List of the mean Chop mRNA expression values in antisense oligonucleotide-treated (second screening round) SKOV-3 cells compared to control antisense oligonucleotide (neg1) treated cells. Expression values are normalized to HPRT1.

| ASO | Residual Chop expression (compared to neg1-treated cells) |
| --- | --- |
| A19003H | 0.39 |
| A19027H | 0.45 |
| A19029H | 0.45 |
| A19018HM | 0.48 |
| A19037H | 0.48 |
| A19001H | 0.50 |
| A19020HM | 0.52 |
| A19004H | 0.52 |
| A19028H | 0.53 |
| A19021HM | 0.56 |
| A19017H | 0.67 |
| A19031HM | 0.69 |
| Control ASO (neg1) | 1.01 |

Example 3: Determination of $IC_{50}$ Values of Selected Chop Antisense Oligonucleotide in EFO-21 Cells The dose-dependent knockdown of Chop mRNA expression by Chop antisense oligonucleotides in EFO-21 cells was investigated and the respective $IC_{50}$ values were calculated. Therefore, EFO-21 cells were treated for three days with the respective antisense oligonucleotide at the following concentrations: 6 µM, 2 µM, 600 nM, 200 nM, 60 nM, 20 nM, 6 nM, 2 nM. After the treatment period, cells were lyzed, Chop and HPRT1 mRNA expression was analyzed using the QuantiGene Singleplex assay (ThermoFisher) and the Chop expression values were normalized to HPRT1 values. A dose-dependent knockdown of Chop mRNA with all tested Chop antisense oligonucleotides was observed (FIG. 5) with $IC_{50}$ values below 500 nM (Table 26):

TABLE 26

Dose-dependent inhibition of Chop mRNA expression in EFO-21 cells by selected Chop antisense oligonucleotides and respective $IC_{50}$ values.

| ASO | $IC_{50}$ (nM) | Inhibition (%) | | | | | | | |
| --- | --- | --- | --- | --- | --- | --- | --- | --- | --- |
| | | 6 µM | 2 µM | 600 nM | 200 nM | 60 nM | 20 nM | 6 nM | 2 nM |
| A19001H | 338.5 | 80.8 | 76.0 | 58.3 | 28.5 | 4.3 | 5.1 | 4.0 | 0.0 |
| A19003H | 252.8 | 81.7 | 74.7 | 61.7 | 41.0 | 6.2 | 13.6 | 0.0 | 0.0 |
| A19018HM | 227.8 | 72.7 | 67.0 | 54.3 | 35.5 | 14.8 | 7.2 | 0.0 | 0.0 |
| A19020HM | 241.8 | 70.5 | 53.6 | 43.8 | 22.9 | 11.1 | 0.0 | 0.0 | 0.0 |
| A19027H | 256.6 | 80.8 | 71.2 | 57.0 | 22.7 | 20.9 | 0.0 | 0.0 | 0.0 |
| A19028H | 263 | 78.1 | 76.6 | 55.0 | 36.2 | 10.6 | 0.0 | 2.2 | 0.0 |
| A19037H | 311.9 | 81.2 | 68.5 | 51.1 | 29.5 | 0.0 | 0.0 | 0.0 | 0.0 |

Example 4: Knockdown of Chop mRNA in Activated Human CD8+ T Cells after Treatment with Chop Antisense Oligonucleotides To test the activity of Chop antisense oligonucleotides in activated immune cells (CD8+ T cells), the antisense oligonucleotide A19018HM (SEQ ID NO.2) was selected. T cells were activated for three days using tetrameric CD2/CD3/CD28 antibody complexes. During the activation period, cells were treated with the control antisense oligonucleotide neg1 or the Chop-specific antisense oligonucleotide A19018HM at a concentration of 5 µM. After the treatment period, cells were lyzed, Chop and HPRT1 mRNA expression was analyzed using the QuantiGene Singleplex assay (ThermoFisher) and the Chop expression values were normalized to HPRT1 values. As shown in FIG. 6, treatment of T cells with the Chop-specific antisense oligonucleotide A19018HM resulted in a residual Chop mRNA expression of 0.45 compared to untreated cells whereas treatment with the control antisense oligonucleotide had no effect.

Example 5: Efficacy Screen of Human/Mouse Cross-Reactive Chop Antisense Oligonucleotides in Murine Cancer Cell Lines (First Screening Round)

Figure 7B:
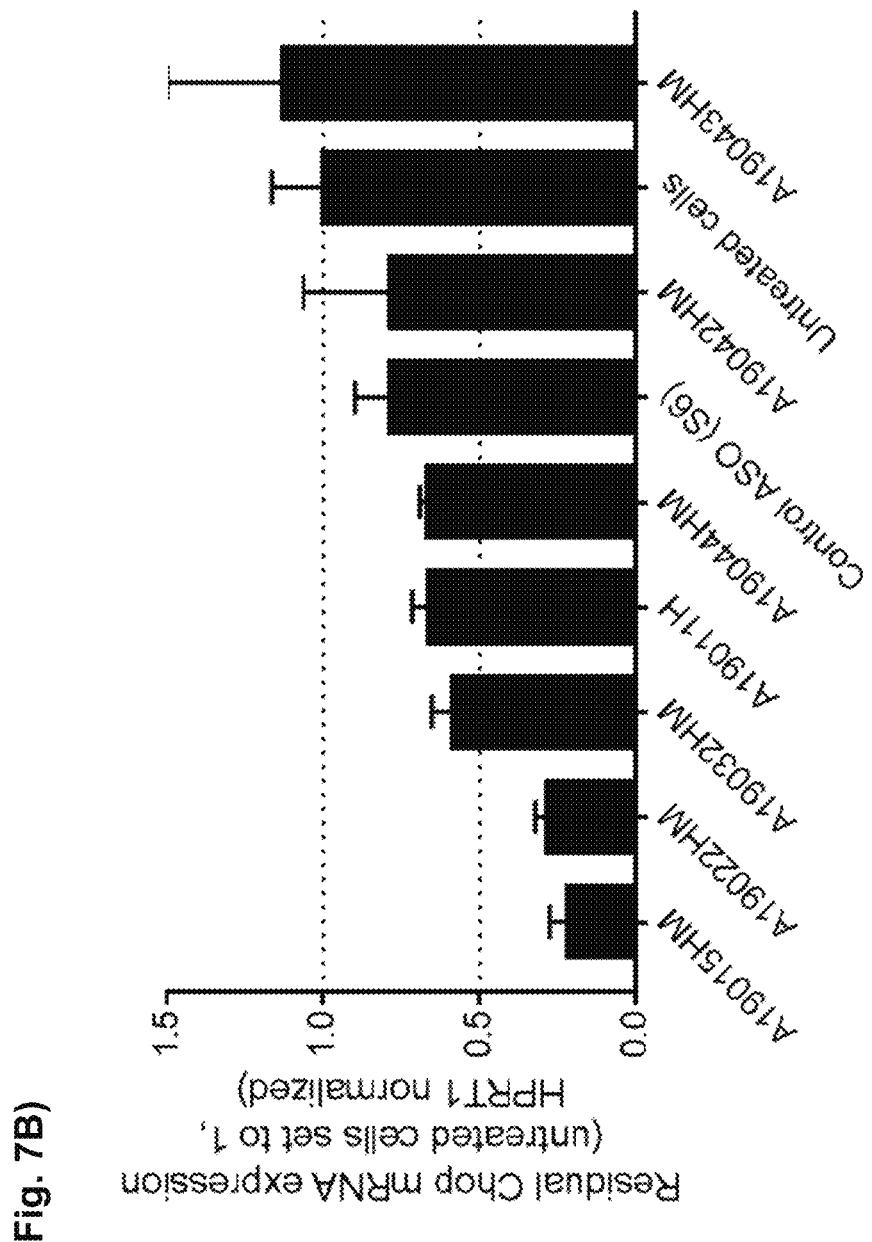

In order to investigate the knockdown efficacy of human/mouse cross-reactive Chop antisense oligonucleotides (Table 1), two efficacy screening rounds were performed in the cancer cell lines Renca (mouse renal adenocarcinoma, ATCC) and 4T1 (tumor of the mammary gland, ATCC). Therefore, cells were treated with the respective antisense oligonucleotide at a concentration of 5 µM for three days without the addition of a transfection reagent. Cells were lyzed after the three days treatment period, Chop and HPRT1 mRNA expression was analyzed using the QuantiGene Singleplex assay (ThermoFisher) and the Chop expression values were normalized to HPRT1 values. The results of the first screening round are shown in FIGS. 7A and 7B as well as in Tables 27 and 28. As shown in FIG. 7A) and Table 27, treatment of Renca cells with the antisense oligonucleotides A19015HM (SEQ ID NO.17), A19022HM (SEQ ID NO.14), A19032HM (SEQ ID NO.24), A19042HM (SEQ ID NO.36), A19043HM (SEQ ID NO.15) and A19044HM (SEQ ID NO.15) resulted in a residual Chop mRNA expression of <0.5 compared to untreated cells. Selected antisense oligonucleotides were furthermore screened in 4T1 cells with regard to their Chop knockdown efficacy. As shown in FIG. 7B) and Table 28, treatment with the antisense oligonucleotides A19015HM and A19022HM resulted in a residual Chop mRNA expression of <0.5 compared to untreated cells. The control antisense oligonucleotide S6 showed only a moderate effect in both tested cell lines.

TABLE 27

List of the mean Chop mRNA expression values in antisense oligonucleotide-treated (first screening round) Renca cells compared to untreated cells. Expression values are normalized to HPRT1.

| ASO | Residual Chop expression (compared to untreated cells) |
|---|---|
| A19022HM | 0.26 |
| A19044HM | 0.37 |
| A19015HM | 0.40 |
| A19032HM | 0.41 |
| A19042HM | 0.46 |
| A19043HM | 0.49 |
| A19009HM | 0.51 |
| A19041HM | 0.52 |
| A19010HM | 0.56 |
| A19039HM | 0.58 |
| A19040HM | 0.59 |
| A19038HM | 0.59 |
| A19005HM | 0.66 |
| Control ASO (S6) | 0.74 |
| A19013HM | 0.85 |
| Untreated cells | 1.01 |

TABLE 28

List of the mean Chop mRNA expression values in antisense oligonucleotide-treated (first screening round) 4T1 cells compared to untreated cells. Expression values are normalized to HPRT1.

| ASO | Residual Chop expression (compared to untreated cells) |
|---|---|
| A19015HM | 0.22 |
| A19022HM | 0.28 |
| A19032HM | 0.58 |
| A19011H | 0.67 |
| A19044HM | 0.67 |
| Control ASO (S6) | 0.78 |
| A19042HM | 0.79 |

TABLE 28-continued

List of the mean Chop mRNA expression values in antisense oligonucleotide-treated (first screening round) 4T1 cells compared to untreated cells. Expression values are normalized to HPRT1.

| ASO | Residual Chop expression (compared to untreated cells) |
|---|---|
| Untreated cells | 1.00 |
| A19043HM | 1.13 |

Example 6: Efficacy Screen of Human/Mouse Cross-Reactive Chop Antisense Oligonucleotides in Murine Cancer Cell Lines (Second Screening Round)

Figure 8B:
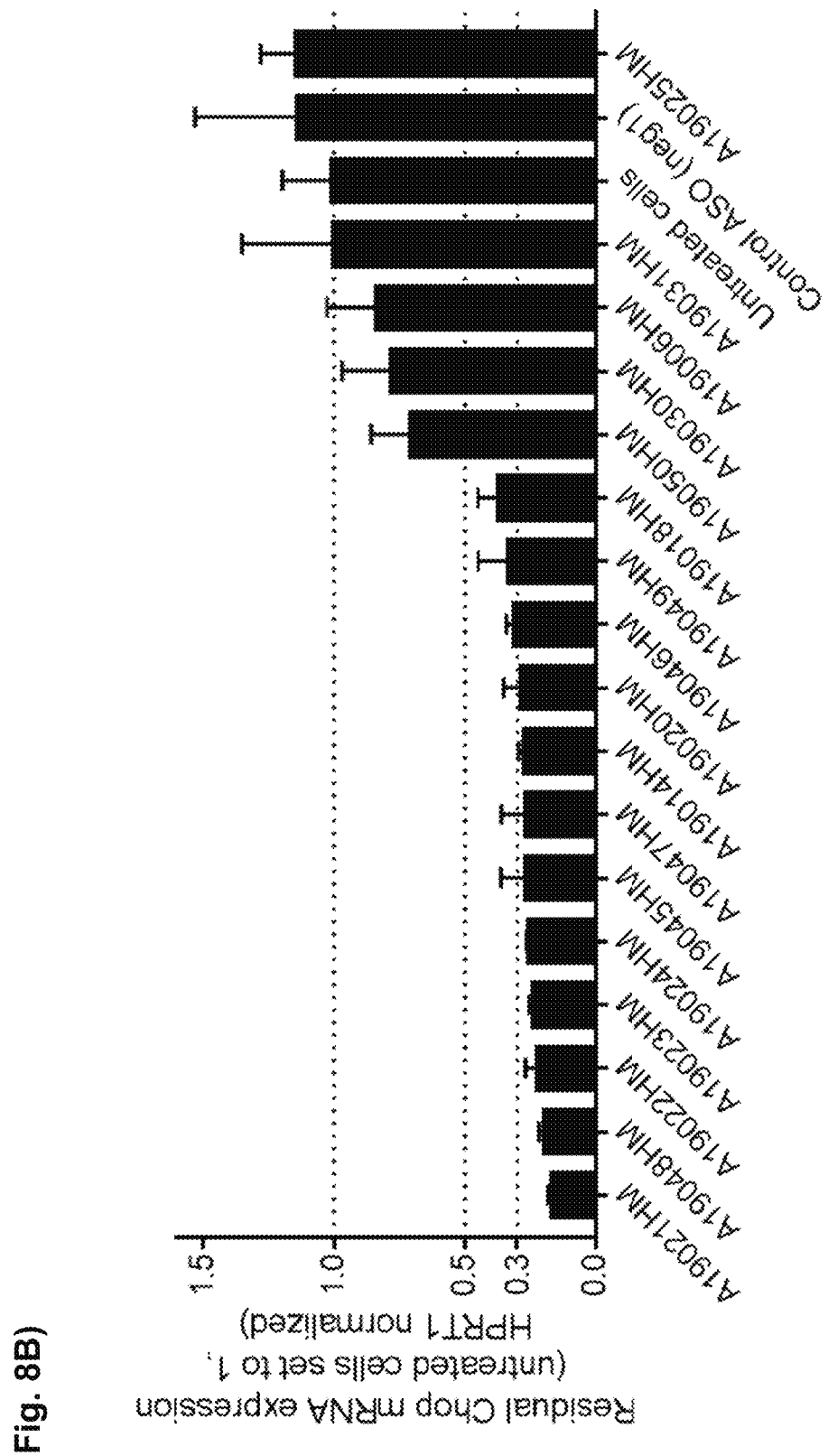

The results of the second screening round are shown in FIGS. 8A and 8B as well as in Tables 29 and 30. As shown in FIG. 8A) and Table 29, treatment of Renca cells with the antisense oligonucleotides A19014HM (SEQ ID NO.32), A19018HM (SEQ ID NO.2), A19020HM (SEQ ID NO.3), A19021HM (SEQ ID NO.20), A19022HM (SEQ ID NO.14), A19024HM (SEQ ID NO.11), A19025HM (SEQ ID NO.39) and A19031HM (SEQ ID NO.10) resulted in a residual Chop mRNA expression of <0.3 compared to untreated cells. Selected antisense oligonucleotides were furthermore screened in 4T1 cells with regard to their Chop knockdown efficacy. As shown in FIG. 8B) and Table 30, treatment with the antisense oligonucleotides A19014HM, A19020HM, A19021HM, A19022HM, A19023HM (SEQ ID NO.33), A19024HM, A19045HM (SEQ ID NO.42), A19047HM (SEQ ID NO.38) and A19048HM (SEQ ID NO.30) resulted in a residual Chop mRNA expression of <0.3 compared to untreated cells. The control antisense oligonucleotide neg1 showed no effect in both tested cell lines.

TABLE 29

List of the mean Chop mRNA expression values in antisense oligonucleotide-treated (second screening round) Renca cells compared to untreated cells. Expression values are normalized to HPRT1.

| ASO | Residual Chop expression (compared to untreated cells) |
|---|---|
| A19018HM | 0.10 |
| A19021HM | 0.12 |
| A19022HM | 0.21 |
| A19031HM | 0.22 |
| A19024HM | 0.24 |
| A19014HM | 0.25 |
| A19020HM | 0.25 |
| A19025HM | 0.27 |
| A19023HM | 0.34 |
| A19047HM | 0.35 |
| A19048HM | 0.36 |
| A19046HM | 0.38 |
| A19045HM | 0.38 |
| A19030HM | 0.43 |
| A19049HM | 0.56 |
| A19050HM | 0.63 |
| A19006HM | 0.64 |
| Control ASO (neg1) | 0.94 |
| Untreated cells | 1.00 |

TABLE 30

List of the mean Chop mRNA expression values
in antisense oligonucleotide-treated (second
screening round) 4T1 cells compared to untreated
cells. Expression values are normalized to HPRT1.

| ASO | Residual Chop expression (compared to untreated cells) |
|---|---|
| A19021HM | 0.16 |
| A19048HM | 0.19 |
| A19022HM | 0.22 |
| A19023HM | 0.24 |
| A19024HM | 0.25 |
| A19045HM | 0.26 |
| A19047HM | 0.27 |
| A19014HM | 0.27 |
| A19020HM | 0.28 |
| A19046HM | 0.31 |
| A19049HM | 0.33 |
| A19018HM | 0.37 |
| A19050HM | 0.70 |
| A19030HM | 0.78 |
| A19006HM | 0.84 |
| A19031HM | 1.00 |
| Untreated cells | 1.01 |
| Control ASO (neg1) | 1.14 |
| A19025HM | 1.14 |

Example 7: Determination of $IC_{50}$ Values of Selected Human/Mouse Cross-Reactive Chop Antisense Oligonucleotides in Renca Cells The dose-dependent knockdown of Chop mRNA expression by Chop antisense oligonucleotides in Renca cells was investigated and the respective $IC_{50}$ values were calculated. Therefore, Renca cells were treated for three days with the respective antisense oligonucleotide at the following concentrations: 6 μM, 2 μM, 600 nM, 200 nM, 60 nM, 20 nM, 6 nM, 2 nM. After the treatment period, cells were lyzed, Chop and HPRT1 mRNA expression was analyzed using the QuantiGene Singleplex assay (ThermoFisher) and the Chop expression values were normalized to HPRT1 values. A dose-dependent knockdown of Chop mRNA with the two tested Chop antisense oligonucleotides A19018HM and A19021HM (FIG. 9) with $IC_{50}$ values below 500 nM (Table 31) was observed.

TABLE 31

Dose-dependent inhibition of Chop mRNA expression in Renca cells by
selected Chop antisense oligonucleotides and respective $IC_{50}$ values

| ASO | $IC_{50}$ (nM) | Inhibition (%) | | | | | | |
|---|---|---|---|---|---|---|---|---|
| | | 6 μM | 2 μM | 600 nM | 200 nM | 60 nM | 20 nM | 6 nM | 2 nM |
| A19018HM | 439.4 | 86.5 | 67.7 | 37.7 | 9.8 | 0 | 0 | 0 | 0 |
| A19021HM | 406.3 | 71.4 | 53.0 | 25.9 | 6.2 | 0 | 0 | 0 | 0 |

Example 8: Knockdown of Chop mRNA in Murine Myeloid Derived Suppressor Cells with Chop Antisense Oligonucleotides Myeloid-derived suppressor cells (MDSC) are one of the major immune cell subset that contribute to the suppressive tumor-microenvironment. Chop seems to play an important role in the regulation of the suppressive capacity of MDSC, as genetic knockout of Chop in those cells has been shown to revert them into immune stimulatory cells in murine model systems (Thevenot et al. 2014). Therefore, it was tested if Chop antisense oligonucleotides have the capacity to knock down Chop in in vitro generated bone marrow-derived MDSC. Murine bone marrow was isolated, cells were plated in tissue culture treated 96-well plates and differentiation to MDSC was induced by addition of granulocyte macrophage colony-stimulating factor (GM-CSF) and macrophage colony-stimulating factor (M-CSF). Cells were additionally treated with the Control antisense oligonucleotide neg1 or the Chop specific antisense oligonucleotide A19018HM at a concentration of 5 μM. Three days later, cells were treated with the N-linked glycosylation inhibitor Tunicamycin in order to mimic stress factors that are present in the tumor-microenvironment as reactive oxygen species (ROS) and nitrogen species (RNS). Tunicamycin as well as ROS and RNS lead to induction of the endoplasmatic reticulum (ER)-stress response including upregulation of Chop. As shown in FIG. 10, treatment of Tunicamycin-treated MDSC with the Chop-specific antisense oligonucleotide A19018HM resulted in a residual Chop mRNA expression of 0.19 compared to cells that had been treated with Tunicamycin but no antisense oligonucleotide (=Untreated cells). Importantly, the Chop mRNA expression in Chop antisense oligonucleotide-treated cells was comparable to cells that had not been treated with Tunicamycin (expression compared to untreated cells: 0.2). Treatment of cells with the control antisense oligonucleotide neg1 had only a moderate negative effect on Chop mRNA expression.

Example 9: Efficacy Screen of Chop Antisense Oligonucleotides in Human Cancer Cell Line In order to investigate the knockdown efficacy of the in silico designed intronic Chop antisense oligonucleotides, an efficacy screening round in the cancer cell line EFO-21 (human Ovarian Cystadenocarcinoma, DSMZ) was performed. Cells were treated with the respective antisense oligonucleotide at a concentration of 5 μM for three days without the addition of a transfection reagent. Cells were lyzed after the three days treatment period, Chop and HPRT1 mRNA expression was analyzed using the QuantiGene Singleplex assay (ThermoFisher) and the Chop expression values were normalized to HPRT1 values. As depicted in FIG. 12 and Table 32, treatment of EFO-21 cells with the antisense oligonucleotides A19072HI, A19071HI, A19066HI, A19054H1 and A19062H1 resulted in a residual Chop RNA expression of <0.6. The control oligonucleotide neg1 showed no effect on Chop RNA expression. A19018HM was used as a reference Chop antisense oligonucleotide that binds to an exonic region of Chop RNA and resulted in a residual Chop RNA expression of 0.55 in this experiment.

TABLE 32

Residual Chop expression in comparison to untreated cells.

| ASO | Residual Chop expression (compared to untreated cells) |
|---|---|
| A19072HI | 0.39 |
| A19071HI | 0.44 |
| A19018HM (reference) | 0.55 |
| A19066HI | 0.57 |
| A19054HI | 0.57 |
| A19062HI | 0.59 |
| A19070HI | 0.63 |
| A19063HI | 0.65 |
| A19067HI | 0.71 |
| A19064HI | 0.72 |
| A19053HI | 0.78 |
| A19055HI | 0.81 |
| A19056HI | 0.81 |
| A19051HI | 0.82 |
| A19052HI | 0.83 |
| A19069HI | 0.84 |
| A19059HI | 0.85 |
| A19061HI | 0.86 |
| A19060HI | 0.87 |
| A19065HI | 0.89 |
| A19058HI | 0.94 |
| A19057HI | 1.08 |
| A19068HI | 1.20 |
| neg1 | 1.00 |

The invention claimed is:

1. Chop inhibitor selected from the group consisting of SEQ ID NO.4, SEQ ID NO.16, SEQ ID NO.18 and a combination thereof, wherein at least one of the nucleotides is modified, and the oligonucleotide hybridizes with a nucleic acid sequence of C/BP-homologous protein (Chop) of SEQ ID NO.1 (human) and/or SEQ ID NO.48 (human).

2. Inhibitor according to claim 1, wherein the modified nucleotide is selected from the group consisting of a bridged nucleic acid such as LNA, cET, ENA, 2'Fluoro modified nucleotide, 2'O-Methyl modified nucleotide and a combination thereof.

3. The inhibitor of claim 1, wherein the oligonucleotide is selected from the group consisting of

+A*+C*+A*T*G*A*T*A*C*G*C*T*C*+A*+G*+T (SEQ ID NO.4),

+A*+C*+A*T*C*A*T*T*G*G*C*A*C*T*+A*+G*+T (SEQ ID NO.16),

+A*+A*+C*A*T*G*A*T*A*C*G*C*T*+C*+A*+G (SEQ ID NO.18), and a combination thereof, wherein + indicates an LNA nucleotide and * indicates a phosphorothioate (PTO) linkage between the nucleotides.

4. The inhibitor of claim 1, wherein the inhibitor inhibits the expression of Chop at a nanomolar or micromolar concentration.

5. A pharmaceutical composition comprising an inhibitor of claim 1 and a pharmaceutically acceptable carrier, excipient, dilutant or a combination thereof.

6. The pharmaceutical composition of claim 5, further comprising a chemotherapeutic such as platinum, gemcitabine, another active agent, another oligonucleotide, an antibody, a HERA fusion protein, a ligand trap, a Fab fragment, a nanobody, a BiTe and/or a small molecule.

7. The pharmaceutical composition of claim 6, wherein the other oligonucleotide, the antibody, a HERA fusion protein, a ligand trap, a Fab fragment, a nanobody, a BiTe and/or the small molecule inhibits or stimulates an immune suppressive factor and/or an immune stimulatory factor.

8. The pharmaceutical composition of claim 7, wherein the immune suppressive factor is selected from the group consisting of IDO1, IDO2, CTLA-4, PD-1, PD-L1, LAG-3, VISTA, A2AR, CD39, CD73, STAT3, TDO2, TIM-3, TIGIT, TGF-beta, BTLA, MICA, NKG2A, KIR, CD160, Chop, Xbp1 and a combination thereof.

9. The pharmaceutical composition of claim 7, wherein the immune stimulatory factor is selected from the group consisting of 4-1BB, Ox40, KIR, GITR, CD27, 2B4 and a combination thereof.

10. A method of treating cancer and/or a nephrological disease such as diabetic nephropathy, the method comprising administering the inhibitor of claim 1 to a subject in need thereof.

11. The method of claim 10, wherein the cancer is breast cancer, lung cancer, malignant melanoma, lymphoma, skin cancer, bone cancer, prostate cancer, liver cancer, brain cancer, cancer of the larynx, gall bladder, pancreas, testicular, rectum, parathyroid, thyroid, adrenal, neural tissue, head and neck, colon, stomach, bronchi, kidneys, basal cell carcinoma, squamous cell carcinoma, metastatic skin carcinoma, osteo sarcoma, Ewing's sarcoma, reticulum cell sarcoma, liposarcoma, myeloma, giant cell tumor, small-cell lung tumor, islet cell tumor, primary brain tumor, meningioma, acute and chronic lymphocytic and granulocytic tumors, acute and chronic myeloid leukemia, hairy-cell tumor, adenoma, hyperplasia, medullary carcinoma, intestinal ganglioneuromas, Wilm's tumor, seminoma, ovarian tumor, leiomyomater tumor, cervical dysplasia, retinoblastoma, soft tissue sarcoma, malignant carcinoid, topical skin lesion, rhabdomyosarcoma, Kaposi's sarcoma, osteogenic sarcoma, malignant hypercalcemia, renal cell tumor, polycythermia vera, adenocarcinoma, anaplastic astrocytoma, glioblastoma multiforma, leukemia, or epidermoid carcinoma.

12. The method of claim 10, wherein the inhibitor or the composition is suitable to be administered locally or systemically.

* * * * *